United States Patent
Granka et al.

(10) Patent No.: US 10,504,611 B2
(45) Date of Patent: Dec. 10, 2019

(54) ANCESTRAL HUMAN GENOMES

(71) Applicant: Ancestry.com DNA, LLC, Lehi, UT (US)

(72) Inventors: Julie M. Granka, San Francisco, CA (US); Keith D. Noto, San Francisco, CA (US)

(73) Assignee: Ancestry.com DNA, LLC, Lehi, UT (US)

(*) Notice: Subject to any disclaimer, the term of this patent is extended or adjusted under 35 U.S.C. 154(b) by 292 days.

(21) Appl. No.: 15/519,105

(22) PCT Filed: Oct. 19, 2015

(86) PCT No.: PCT/US2015/056187
§ 371 (c)(1),
(2) Date: Apr. 13, 2017

(87) PCT Pub. No.: WO2016/061570
PCT Pub. Date: Apr. 21, 2016

(65) Prior Publication Data
US 2017/0277827 A1    Sep. 28, 2017

Related U.S. Application Data

(60) Provisional application No. 62/065,557, filed on Oct. 17, 2014, provisional application No. 62/065,726, filed on Oct. 19, 2014.

(51) Int. Cl.
*G06F 19/00*    (2018.01)
*G16B 20/00*    (2019.01)
(Continued)

(52) U.S. Cl.
CPC ............ *G16B 20/00* (2019.02); *G06F 17/18* (2013.01); *G16B 5/00* (2019.02); *G16B 40/00* (2019.02)

(58) Field of Classification Search
CPC ........ G16B 40/00; G16B 10/00; G16B 20/00; G16B 30/00; G16B 35/00; G16B 5/00;
(Continued)

(56) References Cited

U.S. PATENT DOCUMENTS

2008/0027656 A1    1/2008  Parida
2014/0067355 A1    3/2014  Noto et al.
(Continued)

FOREIGN PATENT DOCUMENTS

WO    WO 2012/099890 A1    7/2012
WO    WO 2014/145280 A1    9/2014
(Continued)

OTHER PUBLICATIONS

Druet et al. 2011: Modeling of Identity-by-Descent Processes Along a Chromosome between Haplotypes and their Genotyped Ancestors. Genetics vol. 188 pp. 409-419.*
(Continued)

*Primary Examiner* — Mary K Zeman
(74) *Attorney, Agent, or Firm* — Fenwick & West LLP

(57) ABSTRACT

Described are computational methods to reconstruct the chromosomes (and genomes) of ancestors given genetic data, IBD information, and full or partial pedigree information of some number of their descendants.

20 Claims, 15 Drawing Sheets

Specification includes a Sequence Listing.

(51) Int. Cl.
    *G16B 5/00*     (2019.01)
    *G16B 40/00*     (2019.01)
    *G06F 17/18*     (2006.01)

(58) Field of Classification Search
    CPC ........ G16B 50/00; G16B 40/20; G16B 40/30;
                G16B 50/10; C12Q 1/6888; G16C 20/60;
                G06F 17/18; G06F 19/18; G06F 19/12;
                G06F 19/24
    See application file for complete search history.

(56) References Cited

U.S. PATENT DOCUMENTS

| | | |
|---|---|---|
| 2014/0278138 A1 | 9/2014 | Barber et al. |
| 2016/0026755 A1 | 1/2016 | Byrnes et al. |

FOREIGN PATENT DOCUMENTS

| | | |
|---|---|---|
| WO | WO 2016/061260 A1 | 4/2016 |
| WO | WO 2016/061568 A1 | 4/2016 |

OTHER PUBLICATIONS

Glazer et al. 2012 Improving Pedigree-based Linkage Analysis by Estimating Coancestry Among Families. Statistical Applications in Genetics and Molecular Biology vol. 11 issue 2 article 11, pp. 1-18.*
Kirkpatrick et al. 2011 Pedigree Reconstruction Using Identity-by-Descent. J Computational Biology vol. 18 No. 11 p. 1481-1493.*
Li et al. 2011 Haplotype Reconstruction in Large Pedigrees with Untyped Individuals through IBD reference. Journal of Computational Biology vol. 18 No. 11 pp. 1411-1421.*
Livne et al. Mar. 3, 2015 PRIMAL: Fast and Accurate Pedigree-based Imputation from sequence data in a Founder Population. PLOS Computational Biology vol. 11 No. 3 e1004139, pp. 1-14.*
Palin et al. 2011 Identity-by-Descent based phasing and imputation in Founder populations using graphical models. Genetic Epidemiology vol. 35 pp. 853-860.*
Speed et al. Jan. 2015 Relatedness in the post-genomic era: is it still useful? Nature Reviews Genetics, vol. 16 pp. 33-45.*
Kenny, E.E. et al., "Increased Power of Mixed Models Facilitates Association Mapping of 10 Loci for Metabolic Traits in an Isolated Population," Human Molecular Genetics, 2011, pp. 827-839, vol. 20, No. 4.
Browning, B. L. et al., "Improving the Accuracy and Efficiency of Identity by Descent Detection in Population Data," Genetics, Jun. 2013, pp. 459-471, vol. 194.
Browning, B. L. et al., "A Unified Approach to Genotype Imputation and Haplotype Phase Inference for Large Data sets of Trios and Unrelated Individuals," The American Journal of Human Genetics, Feb. 13, 2009, pp. 210-223, vol. 84.
Elston, R.C. et al., "A General Model for the Genetic Analysis of Pedigree Data," Human Heredity, 1971, pp. 523-542, vol. 21, No. 6.
Gusev A. et al., "Whole Population, Genomewide Mapping of Hidden Relatedness," Genome Research, 2009, pp. 318-326, vol. 19.
Kong, A. et al. "Detection of Sharing by Descent, Long-Range Phasing and Haplotype Imputation," Nature Genetics, Sep. 2008, pp. 1068-1075, vol. 40, No. 9.
Lander, E.S. et al., "Construction of Multilocus Genetic Linkage Maps in Humans," Proc. Nat. Acad. Sci., Apr. 1987, pp. 2363-2367, vol. 84.
Meuwissen, T. et al., "The Use of Family Relationships and Linkage Disequilibrium to Impute Phase and Missing Genotypes in Up to Whole Genome Sequence Density Genotypic Data," Genetics, Aug. 2010, pp. 1441-1449, vol. 185.
Ott, J., "Estimation of the Recombination Fraction in Human Pedigrees: Efficient Computation of the Likelihood for Human Linkage Studies," American Journal of Human Genetics, 1974, pp. 588-597, vol. 26, No. 5.
Thompson, E. A. "Statistical Inference from Genetic Data on Pedigrees," NSF-CBMS Regional Conference Series in Probability and Statistics, 2000, 186 pages, vol. 6.
Purcell, S. et al., "PLINK: A Tool Set for Whole-Genome Association and Population-Based Linkage Analyses," The American Journal of Human Genetics, Sep. 2007, pp. 559-575, vol. 81.
Browning, B.L. et al., "A Fast, Powerful Method for Detecting Identity by Descent," The American Journal of Human Genetics, Feb. 11, 2011, pp. 173-182, vol. 88.
Williams, A. L. et al., "Phasing of Many Thousands of Genotyped Samples," The American Journal of Human Genetics, Aug. 10, 2012, pp. 238-251, vol. 91.
Browning, S. R., "Multilocus Associate Mapping Using Variable-Length Markov Chains," The American Journal of Human Genetics, Jun. 2006, pp. 903-913, vol. 78.
Browning, S. R. et al., "Rapid and Accurate Haplotype Phasing and Missing-Data Inference for Whole-Genome Association Studies by Use of Localized Haplotype Clustering," The American Journal of Human Genetics, Nov. 2007, pp. 1084-1096, vol. 81.
Durbin, R. M. et al., "A Map of Human Genome Variation from Population-Scale Sequencing," Nature, Oct. 28, 2010, pp. 1061-1073, vol. 467.
Ron, D., et al., "On the Learnability and Usage of Acyclic Probabilistic Finite Automata," Journal of Computer and System Sciences, 1998, pp. 133-152, vol. 56.
Welch, B. L., "The Generalization of "Student's" Problem When Several Different Population Variances are Involved," Biometrika, Jan. 1947, pp. 28-35, vol. 34, Issue 1-2.
Browning, S.R. et al., "Haplotype Phasing: Existing Models and New Developments," Nature Reviews Genetics, Oct. 2011, pp. 703-714, vol. 12.
European Extended Search Report, European Application No. 15851471. 1, dated Mar. 6, 2018, 12 pages.
Li, H. et al., "Relationship Estimation from Whole-Genome Sequence Data," PLOS Genetics, Jan. 30, 2014, p. e1004144, vol. 10, No. 1.
Durand, E.Y. et al., "Reducing Pervasive False-Positive Identical-by-Descent Segments Detected by Large-Scale Pedigree Analysis," Molecular Biology and Evolution, Apr. 30, 2014, pp. 2212-2222, vol. 31, No. 8.
European Extended Search Report, European Application No. 15850985. 1, dated Mar. 6, 2018, 12 pages.
Li, Y. et al., "MaCH: Using Sequence and Genotype Data to Estimate Haplotypes and Unobserved Genotypes," Genetic Epidemiology, Nov. 5, 2010, pp. 816-834, vol. 34, No. 8.
PCT International Search Report & Written Opinion, International Application No. PCT/US2015/056187, dated Jan. 4, 2016, 15 Pages.
Rocchi, M., et al., "Ancestral genomes reconstruction: An integrated, multi-disciplinary approach is needed," Genome Research, 2006, pp. 1441-1444, vol. 16, No. 12.
Thompson, E.A., "Identity by Descent: Variation in Meiosis, Across Genomes, and in Populations," Genetics, 2013, pp. 301-326, vol. 194.

\* cited by examiner

FIG. 5A

Individual 1: A T T A A C A G A A T A A A C
Individual 2: C A T A G A T A G G C
         C T A T G G C C A G G A T
         C T T A G A T A T A G G G C
Inferred:  C T T A G A T A T G G G C Phase flip in individual 1 given inferred haplotype
Inferred ambiguous site

FIG. 5B

True:     A T T A A C A G A A T A A A C
Inferred: a T T A A C A c A A C A ? C

Correct lowercase
Correct uppercase
Lowercase mismatch
Uppercase mismatch
Unknown

SEQUENCE LISTING

```
<160> NUMBER OF SEQ ID NOS: 5

<210> SEQ ID NO 1
<211> LENGTH: 15
<212> TYPE: DNA
<213> ORGANISM: Homo sapiens

<400> SEQUENCE: 1
attaacagaa taaac                                                   15

<210> SEQ ID NO 2
<211> LENGTH: 15
<212> TYPE: DNA
<213> ORGANISM: Homo sapiens

<400> SEQUENCE: 2
cattagatat agggc                                                   15

<210> SEQ ID NO 3
<211> LENGTH: 15
<212> TYPE: DNA
<213> ORGANISM: Homo sapiens

<400> SEQUENCE: 3
ctatggctca aggat                                                   15

<210> SEQ ID NO 4
<211> LENGTH: 15
<212> TYPE: DNA
<213> ORGANISM: Homo sapiens

<400> SEQUENCE: 4
ctttagatat agggc                                                   15
```

-continued

```
<210> SEQ ID NO 5
<211> LENGTH: 15
<212> TYPE: DNA
<213> ORGANISM: Homo sapiens
<220> FEATURE:
<221> NAME/KEY: modified_base
<222> LOCATION: (14)..(14)
<223> OTHER INFORMATION: a, c, t, g, unknown or other

<400> SEQUENCE: 5
attaacacaa caanc                                                         15
```

US 10,504,611 B2

ANCESTRAL HUMAN GENOMES

CROSS REFERENCE TO RELATED APPLICATIONS

This application claims the benefit of U.S. Provisional Application No. 62/065,557, filed Oct. 17, 2014 and U.S. Provisional Application No. 62/065,726, filed Oct. 19, 2014, each which is hereby incorporated in its entirety by reference.

SEQUENCE LISTING

The instant application contains a Sequence Listing which has been submitted electronically in ASCII format and is hereby incorporated by reference in its entirety. Said ASCII copy, created on May 17, 2017, is named 30926US_CRF_sequencelisting.txt and is 1,136 bytes in size.

BACKGROUND

Field

The disclosure relates generally to methods and computer software for reconstruction of ancestral chromosomal sequences using information from descendants including genetic data, identical by descent information, and pedigree information.

Description of Related Art

The genomes of individuals who lived long ago can persist in modern populations in the form of genomic segments broken down by recombination and inherited by their descendants. Reconstruction of ancestral genomes, e.g., ancestral chromosomal sequences, using genotype data from a number of their descendants and relatives has been described (Kong et al. (2008) and Meuwissen and Goddard (2010), Elston and Stewart (1971), Lander and Green (1987), Ott (1974); Thompson (2000)). The previous methods require a full pedigree—i.e., the pedigree relationships between all individuals from whom genetic information has been obtained. In addition, previous methods cannot handle large numbers of genotyped descendants or genetic data from hundreds of thousands of genome-wide markers.

SUMMARY

Described embodiments enable reconstruction of sequences of the chromosomes (and genomes) of an ancestor of interest and partner (an ancestral couple) given genetic data and at least partial pedigree information of some descendants. Genetic data can be, for example, identity of 700,000 genome-wide SNPs for a plurality of individuals. The genetic data is analyzed to generate a set of pairs of individuals, each pair sharing a genomic DNA segment that is identical by descent (IBD). Pedigree data from at least some of the individuals is analyzed to identify a Most Recent Common Ancestor (MRCA) for all pairs in the set of paired individuals, and to identify a particular ancestor of interest of the set of paired individuals. The phased haplotypes of each pair of individuals (corresponding to the shared IBD genomic DNA segment) are compared to generate a set of inferred haplotypes for each IBD genomic DNA segment. The inferred haplotypes are stitched together to generate four phased chromosomal haplotypes belonging to the ancestral couple.

The embodiments do not require a full pedigree linking all genotyped individuals. The embodiments can handle genotypes from any large number of genotyped descendants and can handle genetic data from hundreds of thousands of genome-wide markers. The embodiments are computationally fast and scalable.

BRIEF DESCRIPTION OF THE DRAWINGS

FIG. 5A illustrates comparison of phased haplotypes of individuals and generation of an inferred haplotype in accordance with an embodiment. Figure discloses SEQ ID NOS 1-4 and 4, respectively, in order of appearance.

FIG. 5B compares a true haplotype with an inferred haplotype. Figure discloses SEQ ID NOS 1 and 5, respectively, in order of appearance.

DETAILED DESCRIPTION

Figure 1:
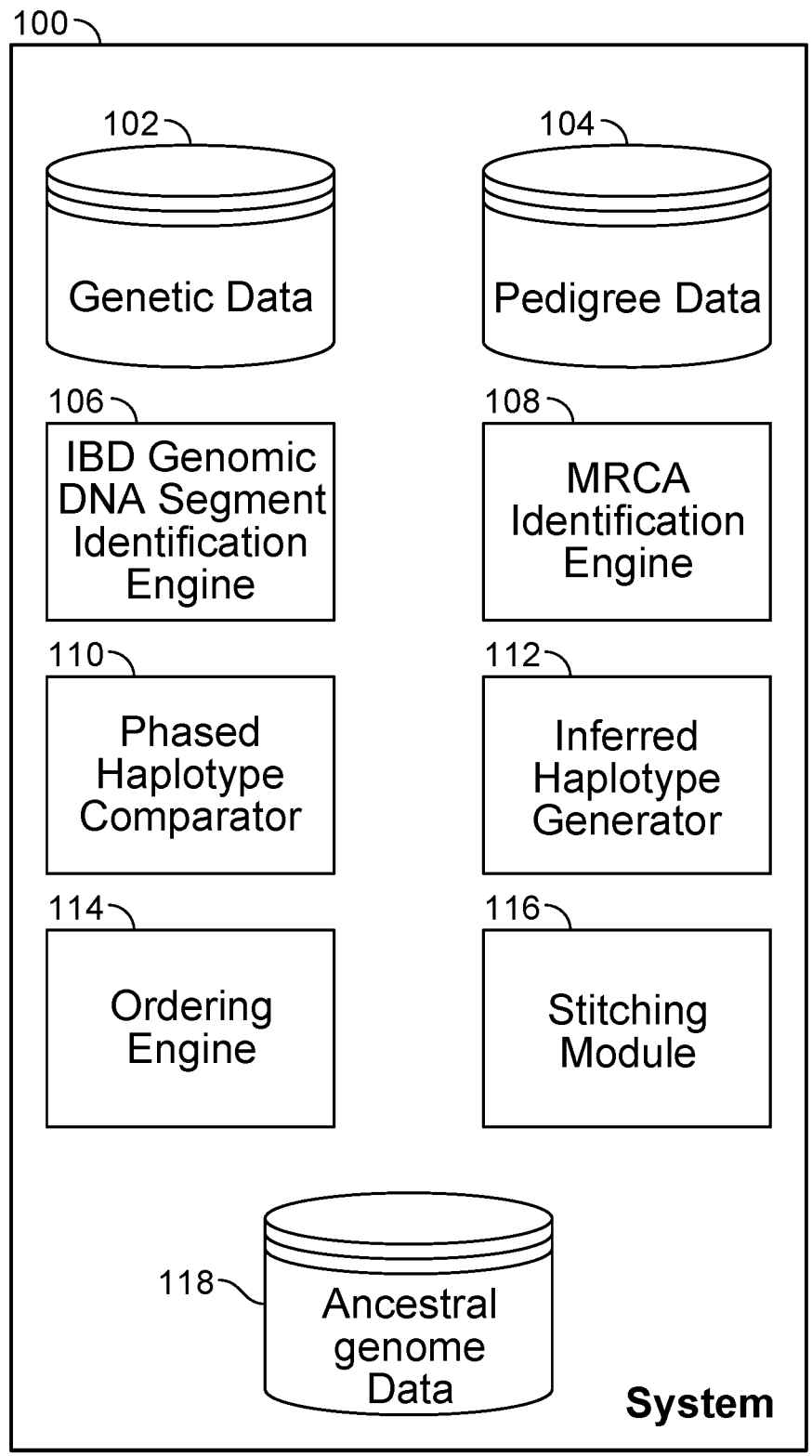
FIG. 1 is a block diagram illustrating components of a system for reconstruction of ancestral chromosomal sequences in accordance with an embodiment.

FIG. 1 illustrates an example system 100 for reconstruction of ancestral chromosomal sequences in accordance with an embodiment. System 100 includes genetic data store 102, pedigree data store 104, IBD genomic DNA segment identification engine 106, MRCA identification engine 108, phased haplotype comparator 110, inferred haplotype generator 112, ordering engine 114, stitching module 116, and ancestral genomes data store 118. Each of these elements is described further below.

Figure 2:
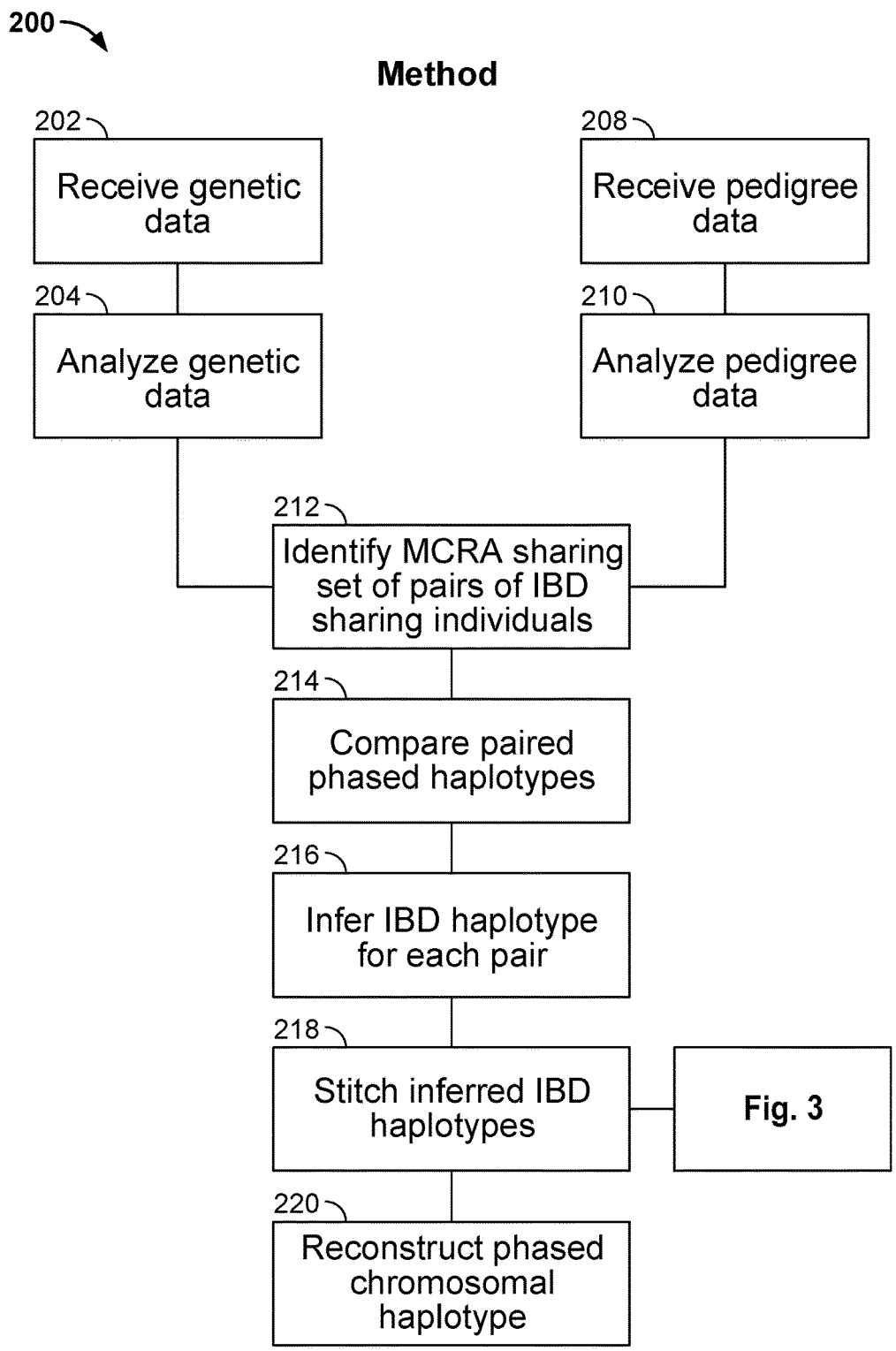
FIG. 2 is a flowchart illustrating a method for reconstruction of ancestral chromosomal sequences in accordance with an embodiment.

FIG. 2 is a flowchart illustrating a method 200 for reconstruction of ancestral chromosomal sequences in accordance with an embodiment and as described in more detail below. The IBD genomic DNA segment identification engine 106 analyses 204 genetic data 102 and MRCA identification engine 108 analyzes 210 pedigree data 104 to identify 212 MRCAs between a set of pair of individuals. Each pair of individuals share an IBD genomic DNA segment; the set of individuals share the MRCA. The MRCA is at least one member of the ancestral couple of interest. Phased haplotype comparator 110 compares 214 the four phased haplotypes belonging to each pair of individuals in the set within each IBD genomic DNA segment. The inferred haplotype generator 112 uses the results of the comparison to infer 216 an inferred haplotype for each pair of individuals. The set of inferred haplotypes are stitched 218 by the stitching module 116 to reconstruct 220 at least one phased chromosomal haplotype. The phased chromosomal haplotype is stored as ancestral genomes data 118.

Genetic Data

System 100 includes genetic data store 102. The reconstruction of ancestral chromosomal sequences in accordance with an embodiment uses genetic data from genetic data store 102 obtained from a plurality of individuals.

The genetic data can be any data well known to one of skill in the art, including genomic DNA sequence data, mRNA sequence data, protein sequence data and the like. The genetic data can be SNP (single nucleotide polymorphism) data, partial sequence data, or complete sequence data. The data can be exome data, restriction fragment length polymorphism (RFLP) data, copy number variant data, or indel data. The genetic data can be from a single locus, from multiple loci or genome-wide. The genetic data can be generated using any method well known to one of skill in the art including but not limited to chips, microarrays, genotyping arrays, or next generation sequencing technologies.

In an embodiment, the genetic data is obtained by genotyping over 700,000 single nucleotide polymorphisms (SNPs) across the human genome obtained using a 730K Illumina OmniExpress Chip.

Identical by Descent DNA

The IBD genomic DNA segment identification engine 106 analyzes the genetic data 102 from a plurality of individuals to identify a set of paired individuals, each pair sharing identical-by-descent (IBD) DNA. IBD genomic DNA segments are pieces of DNA that are identical or nearly-identical in a pair of individuals because both inherited that DNA from a common ancestor.

Figure 4:
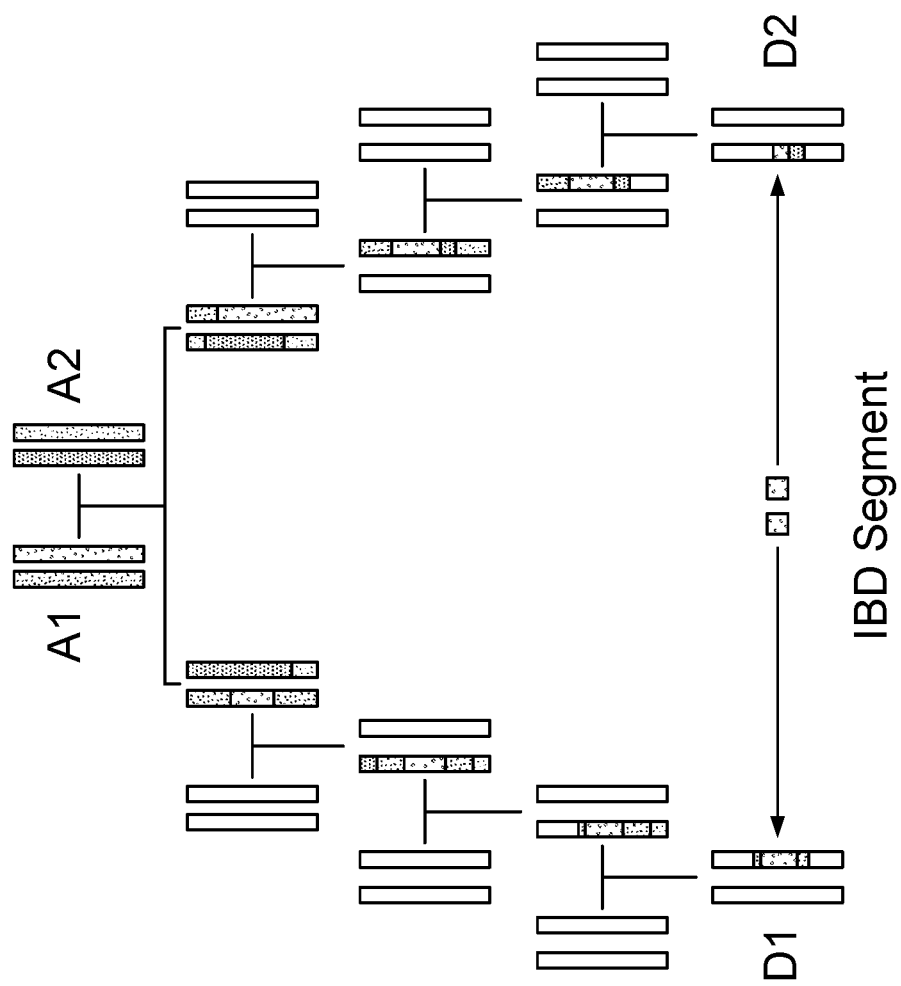
FIG. 4 illustrates chromosomes and IBD DNA of an ancestral couple and their descendants in accordance with an embodiment.

To illustrate this point, FIG. 4 illustrates an example of a pedigree of descendants of two ancestors, Ancestor 1 and Ancestor 2 (A1 and A2). A1 and A2 have two children, who each have children of their own, for a total of four generations—leading to two descendants, D1 and D2. Note that while just one chromosome is shown, the whole genome is made up of 23 pairs of chromosomes. Vertical bars represent the pairs of chromosomes of each individual in the pedigree.

Pieces of the genome where two individuals have inherited the same chunks of DNA from the same ancestor are called identical-by-descent, or IBD. In FIG. 4 the two third cousins (D1 and D2) (4 generations later) at the bottom of the pedigree share DNA identical-by-descent (IBD), in blue, because it was inherited from a common ancestor. The IBD genomic DNA segment represents a piece of Ancestor 1's chromosome. With a large number of descendants, the full genomes of Ancestor 1 and Ancestor 2 could be represented among the descendants and the IBD genomic DNA segments among them.

For two individuals who share DNA identical-by-descent, that DNA they share should represent a piece of the genome of the ancestor from whom they inherited it. However, given that two individuals share DNA identical-by-descent, without a pedigree linking the two individuals, it is not known which ancestor passed down the DNA to both individuals.

There are a variety of available methods used for inferring IBD; any appropriate method may be used.

In an embodiment, inferring the phase of each individual's genotypes is the first step. This means separating the two separate copies of an individual's genome into one that was inherited from their father, and the other that was inherited from their mother. However, which copy was inherited from the father and which from the mother remains unknown. One method used for phasing is UnderDog, described below.

In the second step, regions of the genome that are identical-by-descent between two individuals can be inferred. Again, there are a variety of available methods used to perform this step. One possible method is using JERMLINE (described below), an adaptation of GERMLINE (described in Gusev et. al 2010), with optionally the step of applying TIMBER on these inferred segments (described below).

In another embodiment, other methods are used for finding IBD. One example is RefinedIBD [Browning, B. L. and S. R. Browning, 2013. Improving the Accuracy and Efficiency of Identity by Descent Detection in Population Data. Genetics, 194: 459-471]

Pedigrees and Most Common Recent Ancestors

In an embodiment, pedigree data 104 is analyzed by MRCA identification engine 108 to identify a most common recent ancestor (MRCA) among the set of paired individuals sharing IBD.

A most-recent common ancestor (MRCA) is the most recent ancestor that two individuals share in their direct-line pedigrees. In the example in FIG. 4, the MRCA between D1 and D2 are both A1 and A2. Thus, given a pedigree including A1 and A2, it is known that any IBD genomic DNA segment shared by both D1 and D2 might have been carried by either A1 or A2. However, for any DNA segment they share IBD, that piece only represents one of those two ancestors' chromosomes (in FIG. 4, A1). (However, at another IBD genomic DNA segment, that DNA may represent A2's genome). Aggregating IBD genomic DNA segments among many known descendants of A1 and A2 (in addition to D1 and D2) could thus together represent a large amount of an ancestors' genome.

Pedigree data 104 is associated with at least some individuals in the set, including direct-line relatives and potentially other non-direct line relatives. Pedigree data can be family trees, genealogical data and the like. It is not necessary to have complete pedigree data, e.g., it is not necessary to know the relationships between every individual in the set. Pedigree information can include the names and vital information of an individual's direct and non-direct line ancestors. The methods described herein can be applied to pedigrees of any size and shape.

Given pedigree information for each geno typed individual, the identity of the ancestor contributing the IBD genomic DNA segment is inferred using MRCA identification engine 108. To do so, one searches for MRCA's along the direct ancestral lines of each individual in the pair (i.e. direct-line ancestors of each individual who appear to be the same person based on recorded information in the pedigrees). In an embodiment, the methods disclosed in U.S. patent application Ser. No. 14/214,856 (US 2014/0278138, "Family Networks") incorporated by reference herein in it's entirely are used to identify the MRCA. In other embodiments, the method uses data that is not from a Family Network. All that is needed is a known pedigree structure among individuals (or at the least, the MRCA of all pairs of individuals) in addition to IBD information among those individuals.

In an embodiment, a Family Network is defined by the set of pairs of individuals who all share IBD and the same identified MRCA. The construction of these networks is fully described in International patent application no. PCT/US2014/020014 (WO 2014/145280, "Family Networks").

These networks of descendants of a particular ancestor are created based off of IBD and pedigree information among a large number of individuals. In the construction of a particular ancestor of interest, identified Family Networks of their descendants can be used.

In some embodiments, in addition to providing the set of individuals who are likely descendants of a particular ancestor, Family Networks provide other additional features that are useful in the application of genome reconstruction including pedigree information and Family Network scores.

First, pedigree information collected in the construction of Family Networks provides information including the numbers of common ancestors between two individuals, the identity of those common ancestors, and other important features of pedigree structure that are useful in the methods described herein.

Second, the construction of Family Networks involves the calculation of several relevant scores. One score is the "membership score," which defines one Family Network member's likelihood of being related to other individuals in the network through the identified MRCA. Another score is the "shared ancestor hint score," which defines how likely it is that the DNA that two people share was actually inherited from the MRCA of interest (as opposed to from another common ancestor).

Inferring Haplotypes

System 100 includes a phased haplotype comparator 110 and an inferred haplotype generator 112. The phased haplotype comparator 110 compares the four phased haplotypes from each of two individuals sharing an IBD DNA segment. The inferred haplotype generator 112 determines the alleles of the shared haplotype, producing a set of inferred haplotypes.

A shared IBD DNA segment between two individuals includes the chromosome and start and end coordinates of the segment. However, the actual alleles (or the sequences of DNA) that are shared identical by descent between two individuals are not known. Since each individual has two copies of their genome—one inherited from each parent, the IBD genomic DNA segment shared between two individuals could be shared on either of those two copies of their genome. The next step is to infer which of those copies is shared, i.e. finding the sequence of alleles (or letters) that make up the IBD genomic DNA segment.

One embodiment of this process is illustrated in FIG. 5. Obtaining the haplotype of a IBD DNA segment requires knowing the endpoints of the inferred IBD as well as the inferred phase of each individual involved in the IBD match (i.e., knowing each of their two haplotypes). Turning to FIG. 5A, sequence of each two individuals' phased copies within a hypothetical shared IBD DNA segment is shown. The inferred haplotype is on the bottom row. To infer the match haplotype, the phase of each individual is examined in the region of the IBD DNA segment. The identity of the allele in the inferred haplotype is determined as follows for each SNP along the IBD genomic DNA segment, depending on the alleles present in each individual in one of three conditions:

1. Both individuals homozygous (i.e., A/A and A/A): in this case, the letter at the corresponding position in the haplotype of the match is unambiguous (A).

2. One individual heterozygous (i.e., A/A and A/T): in this case, the letter at the corresponding position in the haplotype of the match is still unambiguous (A).

3. Both individuals heterozygous (i.e. A/T and A/T): in this case, the letter at the corresponding position in the haplotype of the match is ambiguous.

Note that the condition where both individuals are homozygous for alternative alleles is not shown (i.e. A/A and T/T). This is because an IBD match would generally not be inferred between these two individuals under such a scenario. If this does occur, however, a "?" can be shown at this site to indicate the uncertainty in the allele.

To determine the letter of the haplotype in condition 3, the algorithm searches for the nearest SNP where one individual is heterozygous (condition 2), and assigns the letter according to the phase of that haplotype. See an example in FIG. 5A: while the position is A/T and A/T in both individuals, the flanking position to the left (which satisfies condition 2 above) indicates that both the individuals share an "A", which lies on the bottom haplotype of Individual 2. At the position to infer, since Individual 2 has a "T" on the bottom haplotype, a "T" is inferred at the indicated position (indicated by at asterisk in FIG. 5A). If no letter is found that disambiguates the phase within the span of the IBD genomic DNA segment, or if two SNPs at equal distances from the test SNP indicate contradicting alleles at the position, a "?" is assigned to the allele.

An example of an inferred IBD haplotype compared to a true IBD haplotype is shown in FIG. 5B. To differentiate the guessed inference in condition 3 from the unambiguous inferences in conditions 1 and 2, a lower-case letter is returned as output instead of an upper-case letter. (The case of the inferred allele is used in later steps.) In addition to differentiating between alleles by the case of the letter, the algorithm can also assign a score to each inferred letter that is a function of the distance to the nearest unambiguous site.

While the matched haplotype is expected to match one of the individuals' phased haplotypes, this might not always be the case due to errors in phase, IBD estimation, or match haplotype inference. In addition to inferring the haplotype of the match, the algorithm also counts the number of switches between an individual's two haplotypes that are necessary to make the inferred match haplotype consistent. For example, in FIG. 5, no phase flips are necessary in Individual 2 to make the match haplotype consistent (the match haplotype is identical to Individual 2's bottom haplotype). However, one phase flip is required in Individual 1 at the 2nd SNP of the haplotype in order to make the inferred match haplotype consistent. Thus, once the haplotype is inferred, the algorithm scans along the phased haplotypes of each individual, and returns the location of the required phase flips in each individual.

In some embodiments, accuracy of an inferred IBD haplotype is tested by placing inferred alleles of an IBD haplotype into several categories (see FIG. 3), depending on the case of the inferred allele:-Uppercase::Correct (matches the true haplotype)or Incorrect (does not match the true haplotype). Lower case: Correct (a correct guess); Incorrect (does not match the true haplotype); Unknown (an inferred "?").

In some embodiments, scores are assigned to each allele of an IBD haplotype, and the scores can be used in assessing accuracy.

Stitching Algorithm

The system 100 includes a stitching module 116 to analyze the inferred haplotypes and generate ancestral genome data 118 comprising up to four stitched ancestral haplotypes. Ordering engine 114 orders the inferred haplotypes generated by the inferred haplotype generator 112. The stitching module 116 uses the ordered inferred haplotypes to generate or "stitch" together the four stitched ancestral haplotypes. Stitching proceeds by iterating through each IBD genomic DNA segments. In some embodiments, this analysis is performed on one chromosome at a time.

Turning to FIG. FA, a hypothetical example is presented illustrating a list of pairs of individuals who: i) who have the ancestor of interest as their MRCA; ii) who share IBD genomic DNA segments, and iii) for whom the inferred haplotypes have been generated. Inferred haplotypes are all shown in gray, but represent inferred haplotypes as shown in FIG. 5A and FIG. 5B. The inferred haplotypes have been ordered by an ordering engine; here by location and length. It is understood that this example is meant to be illustrative only.

Figure 6A:
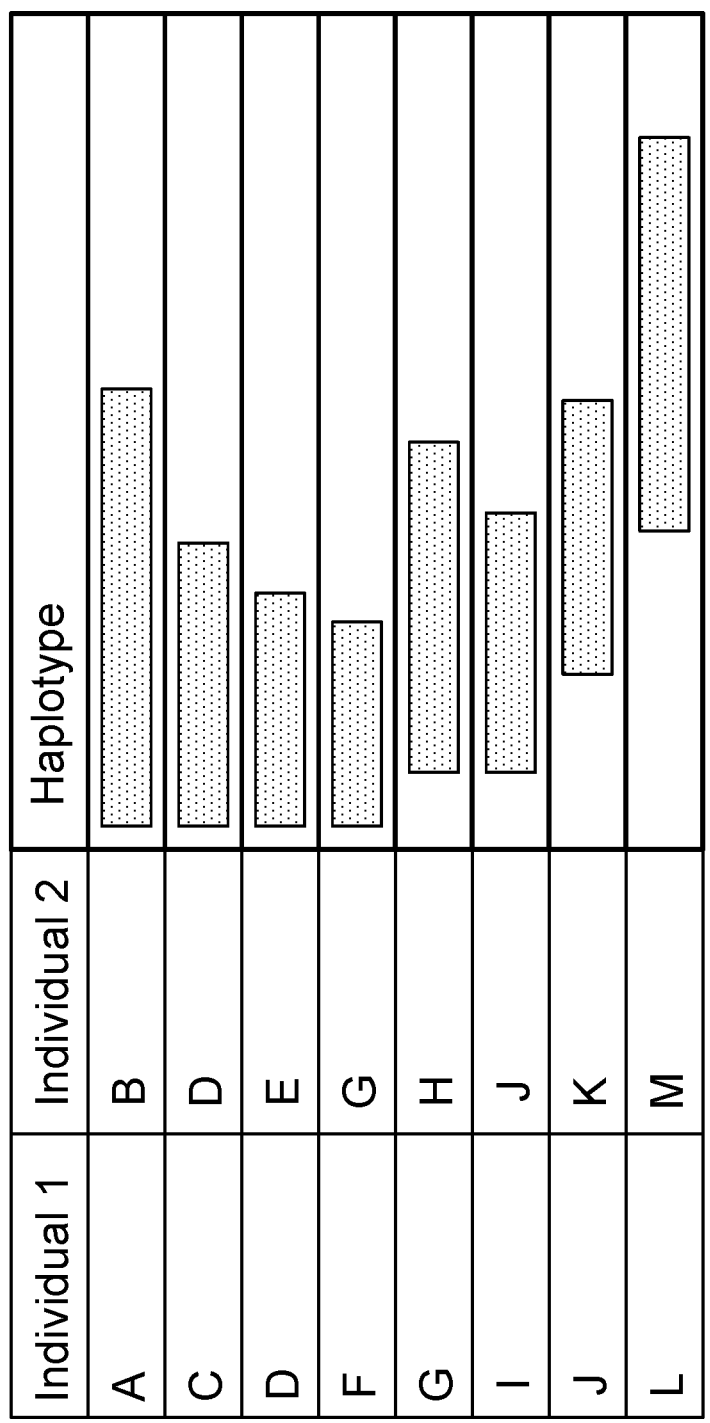
FIG. 6A illustrates a method for stitching together inferred haplotypes in accordance with an embodiment.
Figure 6B:
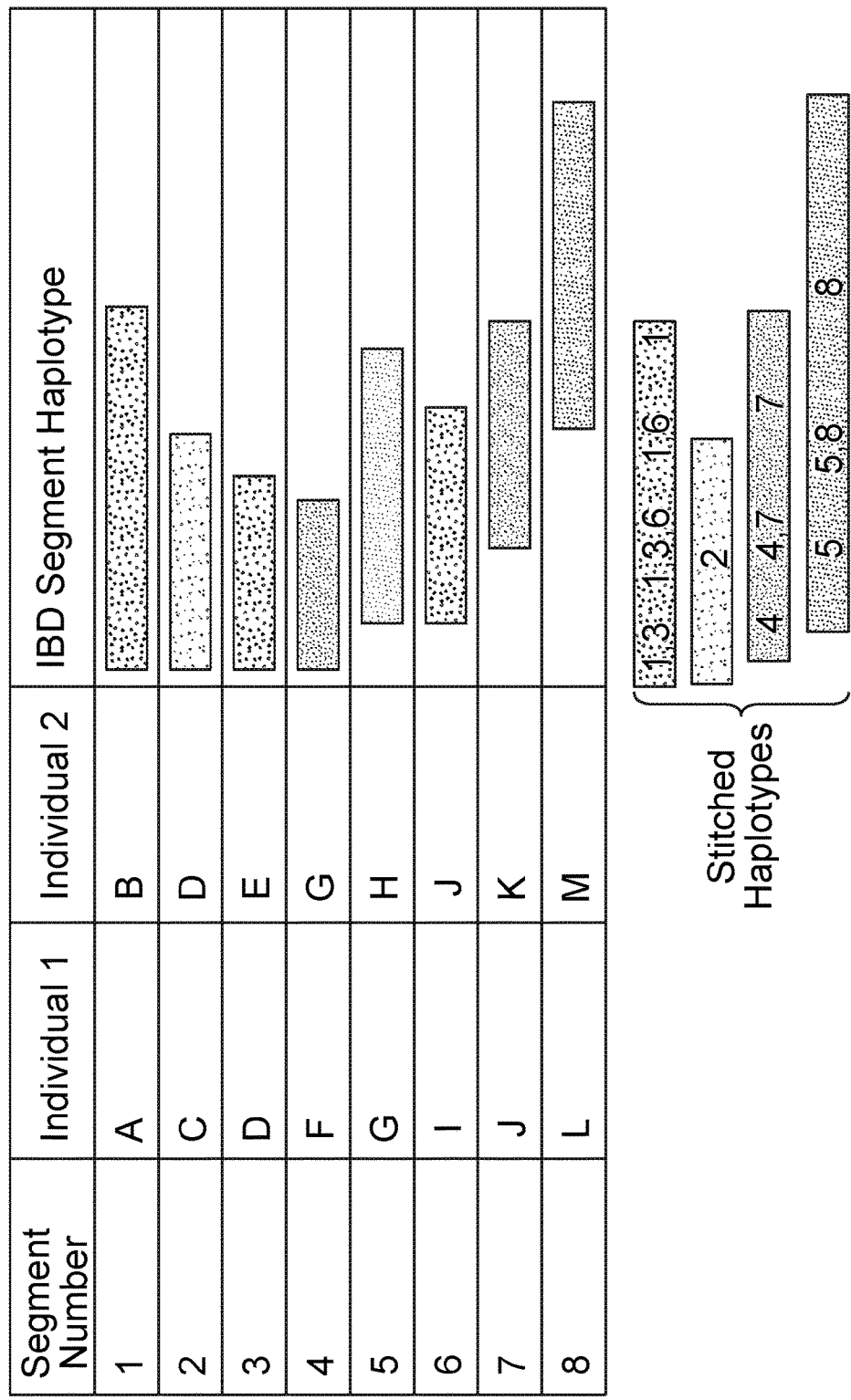
FIG. 6B illustrates a method for stitching together inferred haplotypes in accordance with an embodiment.

Turning to FIG. 6B, the inferred haplotypes of FIG. 6A are now colored in FIG. 6B by the ancestor of origin for clarity, although the ancestral origin is not known. A demonstration of an embodiment of the stitching algorithm is shown. Each inferred haplotype is assessed (here, from top to bottom in the table) and either begins a new path, i.e., stitched ancestral haplotype, or is appended to an existing path depending on identity (here, the color of the segment). The final stitched ancestral haplotype and the identity of the IBD genomic DNA segment making up the paths are shown below the table in FIG. 6B. Locations in a path where two segments are separated by a comma indicate a location where two inferred haplotypes were "stitched."

Figure 3:
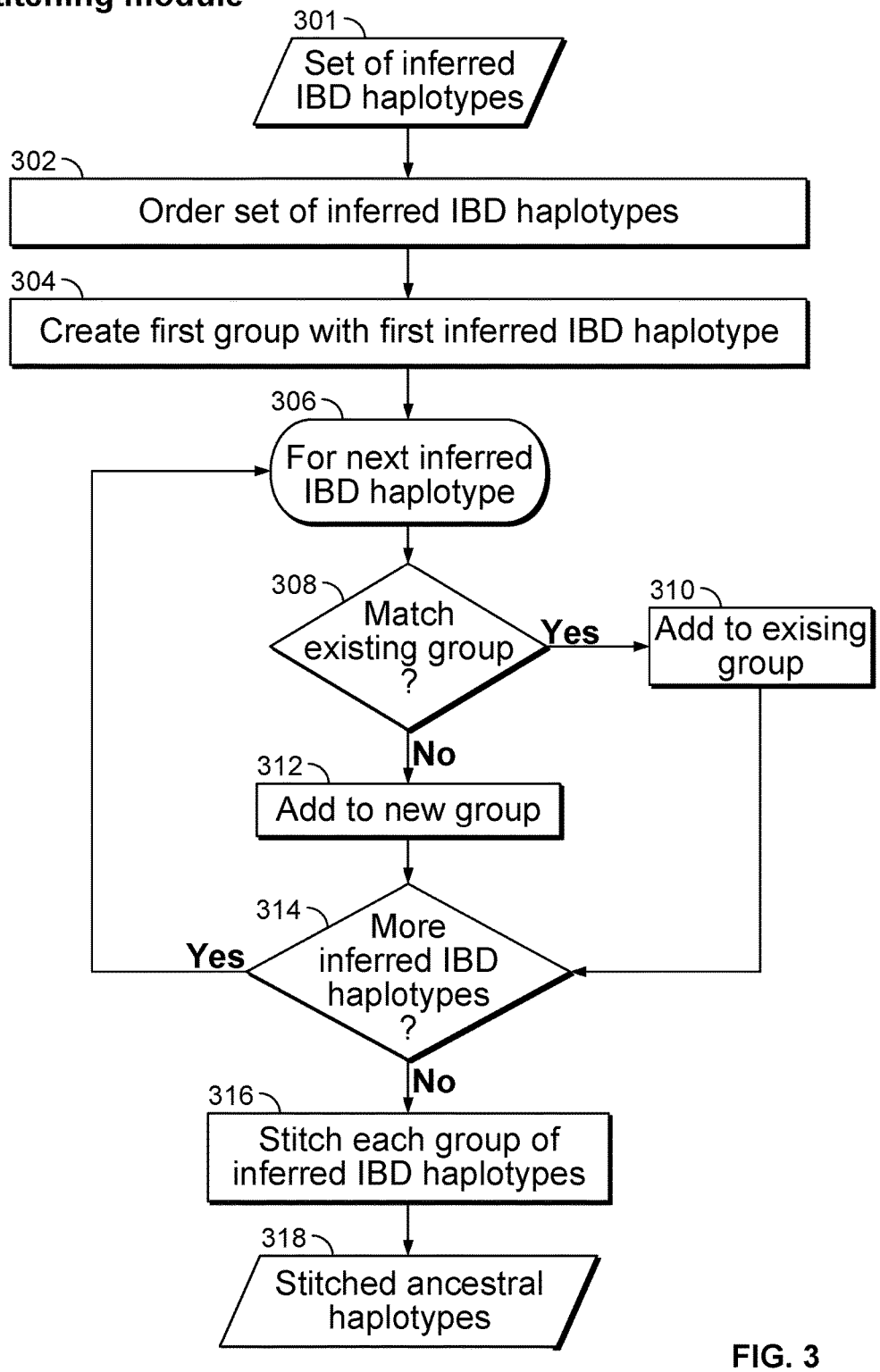
FIG. 3 is a flowchart illustrating a method for stitching inferred haplotypes in accordance with an embodiment.

In an embodiment, the stitching method encompasses the steps as illustrated in FIG. 3 and as described in more detail below. The set of inferred IBD haplotypes 301 is ordered 302, using, e.g., the ordering engine 114. A first group is created 304 with the first inferred IBD haplotype. The next inferred IBD haplotype is compared to the first group to determine if there is a match (308), e.g., if there is overlap and sequence identity within the overlap. If there is a match, the first and next inferred IBD haplotypes are grouped together 310. If there is not a match, a new group is created (312) with the next inferred IBD haplotype. The process is repeated for each inferred IBD haplotype in the ordered set, resulting in groups of inferred IBD haplotypes. Each group is stitched 316 to form a set of stitched ancestral haplotypes 318. Stitching extends the sequence of the first inferred IBD haplotype with the sequence(s) of other inferred haplotypes in the group. In some embodiments, post-processing occurs by merging any stitched haplotype based on predetermined criteria.

In some embodiments, each stitched ancestral haplotype is associated with a score. This score can be based on a combination of any of the following features: number of inferred IBD haplotypes involved in the stitched haplotype; summed length of inferred IBD haplotypes involved in the stitched haplotype; summed score of inferred IBD haplotype involved in the stitched ancestral haplotype (e.g., Family Network scores); summed amount of overlap of IBD DNA segments in a stitched ancestral haplotype; summed amount of identity of IBD DNA segments in a stitched ancestral haplotype (i.e., penalize for errors in identity.

In some embodiments, the method can include pre-filtering the set of IBD genomic DNA segments before ordering. Several statistics may be used to pre-filter the segments used as input for the stitching algorithm. These may include filters based on any combination of the following: Lengths of IBD genomic DNA segments (either in centiMorgans (cM), base-pair, or number of markers) that lie within a pre-specified range (greater than a particular value, and/or less than a particular value.); scores obtained from the Family Network algorithm that lie within a pre-specified range including membership scores for a given individual, as well as shared ancestor hint scores for pairs of individuals involved in the IBD genomic DNA segments; numbers of common ancestors shared between individuals (as inferred from comparing the individuals' pedigrees); other scores for individual IBD genomic DNA segments which assess the agreement between pedigree- and genetically-inferred degrees of relationship.

Ordering and Matching

The method includes ordering the set of inferred IBD haplotypes 302. Ordering methods depend on the application. A simplest ordering is ordering inferred IBD haplotypes from left to right along a chromosome (from smallest base pair start position to largest base pair start position), and further ordering these inferred IBD haplotypes by length—such that the longest segments at a particular start position are added to the model first. Alternatively, inferred IBD haplotypes could be added from right to left, and results from each ordering could be compared.

Inferred IBD haplotypes can also be ordered by the amount of overlap between IBD genomic DNA segments, such that those that overlap the most are added first. This would involve calculating a pairwise distance matrix of amount of overlap among all inferred IBD haplotypes. As IBD haplotypes are added, this pairwise matrix could be updated, or remain static over the course of the stitching algorithm.

Inferred IBD haplotypes can also be ordered by other features, including length of IBD genomic DNA segments in decreasing order, or by features of the Family Network (i.e., sorting segments by individuals' membership scores or shared ancestor hint scores in decreasing order).

The next inferred IBD haplotype is compared to the first group to determine if there is a match (308), e.g., if there is overlap and sequence identity within the overlap. Depending on the data application, different thresholds for the amount of overlap of inferred IBD haplotypes may be used before checking for sequence identity of the inferred IBD haplotypes. Amount of overlap can be thresholded by the number of overlapping markers, the number of overlapping base pairs, or number of overlapping cM; exact thresholds can vary depending on application.

A match also includes a threshold of sequence identity. As used herein, sequence identity includes both partial and complete sequence identity. Several criteria can be used to assess whether or not two overlapping inferred IBD haplotypes have sequence identity. In an embodiment of sequence identity an inferred IBD haplotype with an unknown allele ("?") is defined as identical to all other letters (both upper and lower case). In another embodiment, sequence identity includes exact identity of letters, e.g., nucleotides (ignoring the case of inferred haplotypes) (e.g., the compared inferred IBD haplotypes must have a "G" and a "G" or a "G" and a "g"). In another embodiment, sequence identity includes mismatches at lower case letters (e.g., define "G" as identical to a lower-case "c"; and define lower-case "g" as identical to a lower-case "c"). In another embodiment, sequence identity includes mismatches at upper-case letters (e.g., define "G" as identical to "C").

In some embodiments, criteria for sequence identity allows only fewer than a specified threshold of either upper or lower-case mismatches (either as a function of total number of overlapping markers, of cM length, or of base-pair length).

Adding and Stitching

If there is a match based on overlap and sequence identity as described herein, the inferred IBD haplotype is added to an existing group 310. Each group is stitched 316 to form a set of stitched ancestral haplotypes 318.

In some embodiments the stitched ancestral haplotypes are modified and extended as each inferred IBD haplotype is added to the group. When modifying existing stitched ancestral haplotypes after a "match" (e.g., sequence identity) is determined, several criteria are used.

i. If the inferred IBD haplotype has a "?", update the stitched ancestral haplotypes with a letter (either upper case or lower case), if one is available.

ii. If the inferred IBD haplotype has a lower-case letter, preferentially update the stitched ancestral haplotype with the upper-case letter.

iii. If the upper-case letters are mismatched, greedily keep the first upper-case letter for that stitched ancestral haplotype.

iv. If the lower-case letters are mismatched, greedily keep the first lower-case letter for that stitched ancestral haplotype.

Depending on requirements of conservativeness of the approach, these criteria can be modified.

In some embodiments, instead of modifying the stitched ancestral haplotypes themselves, the groups that are created keep track of the inferred IBD haplotypes that comprise them. This avoids making the "greedy" algorithmic decision to modify stitched ancestral haplotypes based on the first observation, and would require a post-processing of path information as described herein.

In some embodiments, an inferred IBD haplotype may overlap and be identical to multiple existing stitched ancestral haplotypes. To select the stitched ancestral haplotype to modify, a combination of any of the following criteria can be used:

Select the stitched ancestral haplotype with the highest score

Select the stitched ancestral haplotype with the greatest overlap

Select the stitched ancestral haplotype with the greatest identity

In some embodiments, these criteria cannot differentiate between the stitched ancestral haplotypes. Given a tie, multiple greedily could be updated, or the inferred IBD haplotype can be ignored until post-processing as described herein, or the inferred IBD haplotype can be added to all groups.

In some embodiments, post-processing of the stitched ancestral haplotypes can be performed. For example, if upper-case mismatches are not allowed when inferred IBD haplotypes are added to a group or stitched ancestral haplotype, a post-processing step that merges stitched ancestral haplotypes allowing for a set number of upper-case mismatches can be performed. In addition, if inferred IBD haplotypes are ordered in a non-location-based order (see detail 2), a post-processing step that merges stitched ancestral haplotypes under any of the criteria described herein can be used.

In some embodiments, inferred IBD haplotype data contributing to a stitched ancestral haplotypes are stored along with the stitched ancestral haplotypes. Post-processing can be performed to condense stitched ancestral haplotype information across multiple inferred IBD haplotypes. This could be done by determining the consensus alleles across the stitched ancestral haplotypes (i.e., finding the most common allele), or using another statistical approach.

In some embodiments, the stitching method includes selection of the highest quality stitched ancestral haplotypes as those representing the ancestral chromosomes of interest. For example, at any point in the genome, a maximum of four paths should be identified representing the four ancestral haplotypes (see FIG. D). In the case that more than four stitched ancestral haplotypes are identified, stitched ancestral haplotypes can be selected using the score of each stitched ancestral haplotypes as described herein. These scores can be used to assign a "confidence" to each stitched ancestral haplotype to define the likelihood that that stitched ancestral haplotype represents one of the ancestral haplotypes of interest. Given score, the top 4 paths could be selected, or paths above a set threshold can be selected.

Additional Post-processing

In some embodiments, additional post-processing can be performed. This can accomplish several goals including filling gaps in reconstruction; determining the ancestor of origin of a given haplotype (either the father or the mother, see FIG. 4), and/or selecting high-quality paths.

In some embodiments, filling small gaps in the reconstruction can be performed by assessing the likelihood of different combinations of flanking haplotypes using the UnderDog algorithm (as described below). The gaps that can be filled by this approach can be small (on the order of 1-5 cM in length) or larger. UnderDog can be used to perform SNP imputation on these gaps to provide a guess of the likely SNP alleles of the haplotype, as well as an estimate of whether the two haplotypes flanking a gap should be joined.

In some embodiments, determining the ancestor of origin (mother or father) of a given stitched ancestral haplotype, is performed. In some cases, the individual of origin of a particular stitched ancestral haplotypes can be determined using other stitched ancestral haplotypes from other ancestors of interest. This requires having pedigree information and IBD information among descendants of these other ancestors, as well as knowing the relationship between the ancestor of interest and the other reconstructed ancestors and using the methods described herein..

For example, if the genome of Ancestor 1's parents were reconstructed using the described methods, paths could be compared to identify whether a particular path belongs to Ancestor 1 or his wife:

If a path present in a couple's reconstructed paths is present in one of the paths of Ancestor 1's parents, that particular path likely belongs to Ancestor 1, not Ancestor 2 (and vice versa for Ancestor 2's parents). The process of elimination can be used to attribute paths to either ancestor.

In order to determine "identity" of two stitched paths, the various criteria described herein could be applied, depending on depth of the ancestor and desired accuracy.

Various confidence levels can be assigned to these assessments. For example, if genomic coverage of reconstructed paths across a particular region is high, accuracy of the attribution to one individual or another can be given a higher confidence score.

Using this approach, not all paths will be able to be attributed to a given ancestor. For example, if a path is not found in Ancestor 1's parents, it could either belong to Ancestor 2 or still belong to Ancestor 1—thought it did not happen to be reconstructed for Ancestor 1's parents.

As another example, if one of the ancestors had multiple partners or spouses, the method can be used to tease apart the likely ancestor to which the stitched ancestral haplotype belongs. This would involve finding stitched ancestral haplotypes involving at least one IBD genomic DNA segment between two individuals sharing only the ancestor of interest as an MRCA (having been descended from different spouses). Such stitched ancestral haplotypes would likely only represent the ancestor, not one of the two spouses.

Alternative Embodiments

Although this description has been provided in the context of specific embodiments, those of skill in the art will appreciate that many alternative embodiments may be inferred from the teaching provided. Furthermore, within this written description, the particular naming of the components, capitalization of terms, the attributes, data structures, or any other structural or programming aspect is not mandatory or significant unless otherwise noted, and the mechanisms that implement the described invention or its features may have different names, formats, or protocols. Further, some aspects of the system may be implemented via a combination of hardware and software or entirely in hardware elements. Also, the particular division of functionality between the various system components described here is not mandatory; functions performed by a single module or system component may instead be performed by multiple components, and functions performed by multiple components may instead be performed by a single component. Likewise, the order in which method steps are performed is not mandatory unless otherwise noted or logically required.

In addition to the embodiments specifically described above, those of skill in the art will appreciate that the invention may additionally be practiced in other embodiments. Within this written description, the particular naming of the components, capitalization of terms, the attributes, data structures, or any other programming or structural aspect is not mandatory or significant unless otherwise noted, and the mechanisms that implement the described invention or its features may have different names, formats, or protocols. Further, the system may be implemented via a combination of hardware and software, as described, or entirely in hardware elements. Also, the particular division of functionality between the various system components described here is not mandatory; functions performed by a single module or system component may instead be performed by multiple components, and functions performed by multiple components may instead be performed by a single component. Likewise, the order in which method steps are performed is not mandatory unless otherwise noted or logically required. It should be noted that the process steps and instructions of the present invention could be embodied in software, firmware or hardware, and when embodied in software, could be downloaded to reside on and be operated from different platforms used by real time network operating systems.

Algorithmic descriptions and representations included in this description are understood to be implemented by computer programs. Furthermore, it has also proven convenient at times, to refer to these arrangements of operations as modules or code devices, without loss of generality.

Unless otherwise indicated, discussions utilizing terms such as "selecting" or "computing" or "determining" or the like refer to the action and processes of a computer system, or similar electronic computing device, that manipulates and transforms data represented as physical (electronic) quantities within the computer system memories or registers or other such information storage, transmission or display devices.

The present invention also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, DVDs, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and displays presented are not inherently related to any particular computer or other apparatus. Various general-purpose systems may also be used with programs in accordance with the teachings above, or it may prove convenient to construct more specialized apparatus to perform the required method steps. The required structure for a variety of these systems will appear from the description above. In addition, a variety of programming languages may be used to implement the teachings above.

Finally, it should be noted that the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention.

EXAMPLES

Below are examples of embodiments for carrying out the methods described herein. The examples are offered for illustrative purposes only, and are not intended to limit the scope of the present invention in any way.

The methods and systems described herein were used to reconstruct the ancestral genome of an ancestral couple using a test dataset.

UnderDog methods and systems are described in International patent application no. PCT/US2015/056164, filed on Oct. 19, 2015, Timber methods and systems are described in International patent application no. PCT/US2015/055579 filed on Oct. 14, 2015. Jermline methods and systems are described in U.S. patent application Ser. No. 14/029,765, filed Sep. 17, 2013. The contents of these three applications are incorporated by reference in their entirely for all purposes.

Figure 6C:
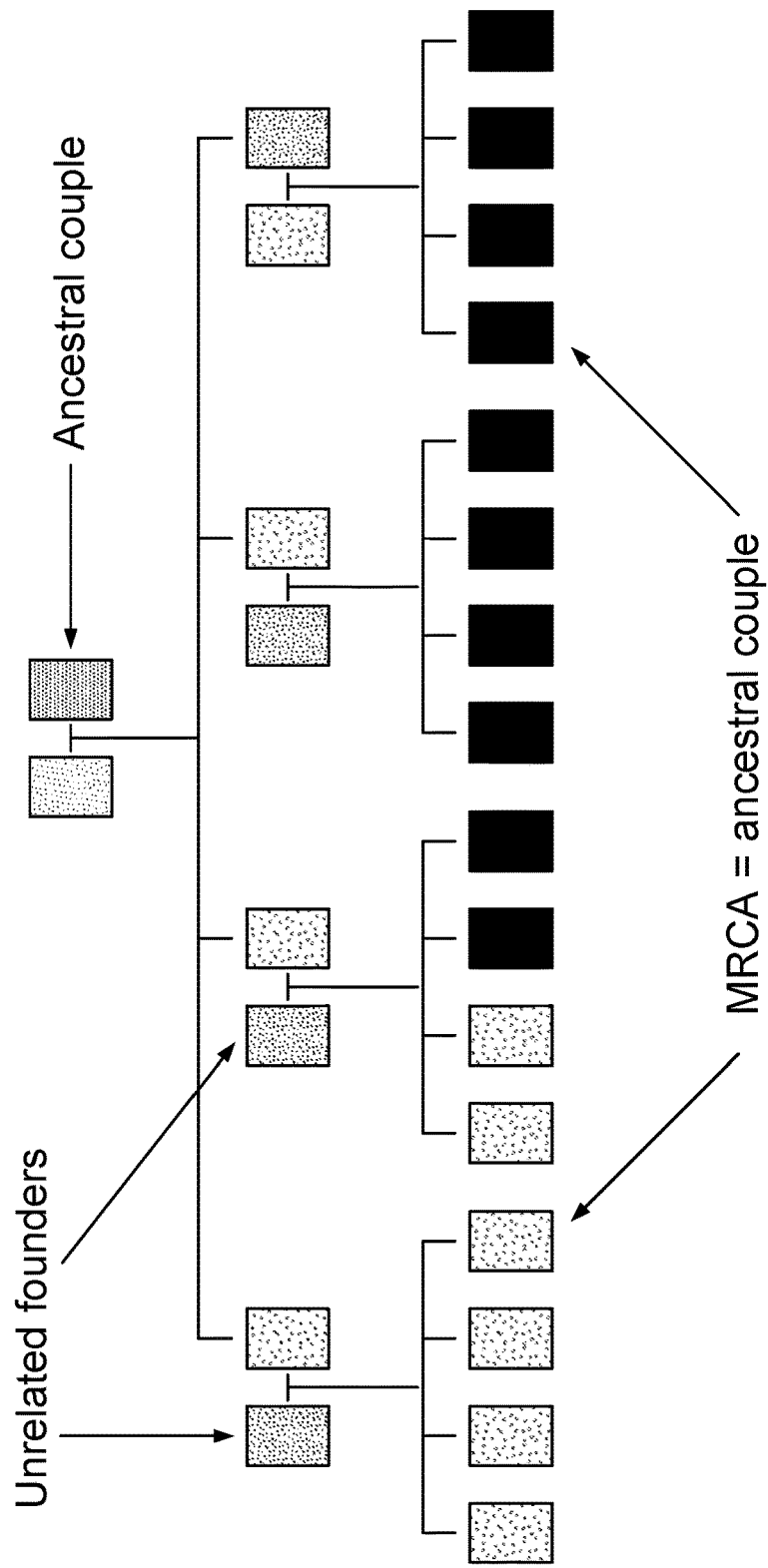
FIG. 6C illustrates a simulated pedigree.

For the test dataset, a 2-generation pedigree was simulated, where each couple in the pedigree has 4 children. The simulated pedigree data is illustrated in FIG. 6C.

Data were simulated using pre-phased data (using trio phasing) for unrelated founder individuals (gray individuals and the ancestral couple in above pedigree), and are mated in silico (using known recombination distances) with other founders, or with children of those founders. This produced true phased data as well as genotype data for a set of descendants, as well as knowledge of the true IBD genomic DNA segments between all individuals.

When applying the described method, several different versions of the simulated data were used:

1. True phase and true IBD endpoints (known from simulations);

2. inferred phase (inferred using UnderDog), true IBD endpoints (known from simulations);

3. Inferred phase (inferred using UnderDog), inferred IBD segments (here, inferred using JERMLINE or GERMLINE and other modifications described herein);

4. Inferred phase (inferred using UnderDog), inferred IBD segments (here, inferred using JERMLINE or GERMLINE and other modifications (described herein), with 96 SNPs trimmed from each end of the IBD segment).

On each of these datasets, the inference of the matching haplotype was made, and the stitching algorithm was run. For the algorithm, only IBD segments between individuals whose most recent common ancestor is the ancestral couple (in above figure) were examined. Details of the parameters used in the stitching algorithm are provided in Section A below.

A. Matching Haplotype Inference

The accuracy of haplotypes that were inferred using the method described herein was assessed.

True phase, true IBD endpoints: No errors of any kind are identified in the inferred haplotypes of the match when true phase and true IBD endpoints are known. As expected, some "?" were inferred.

Figure 7:
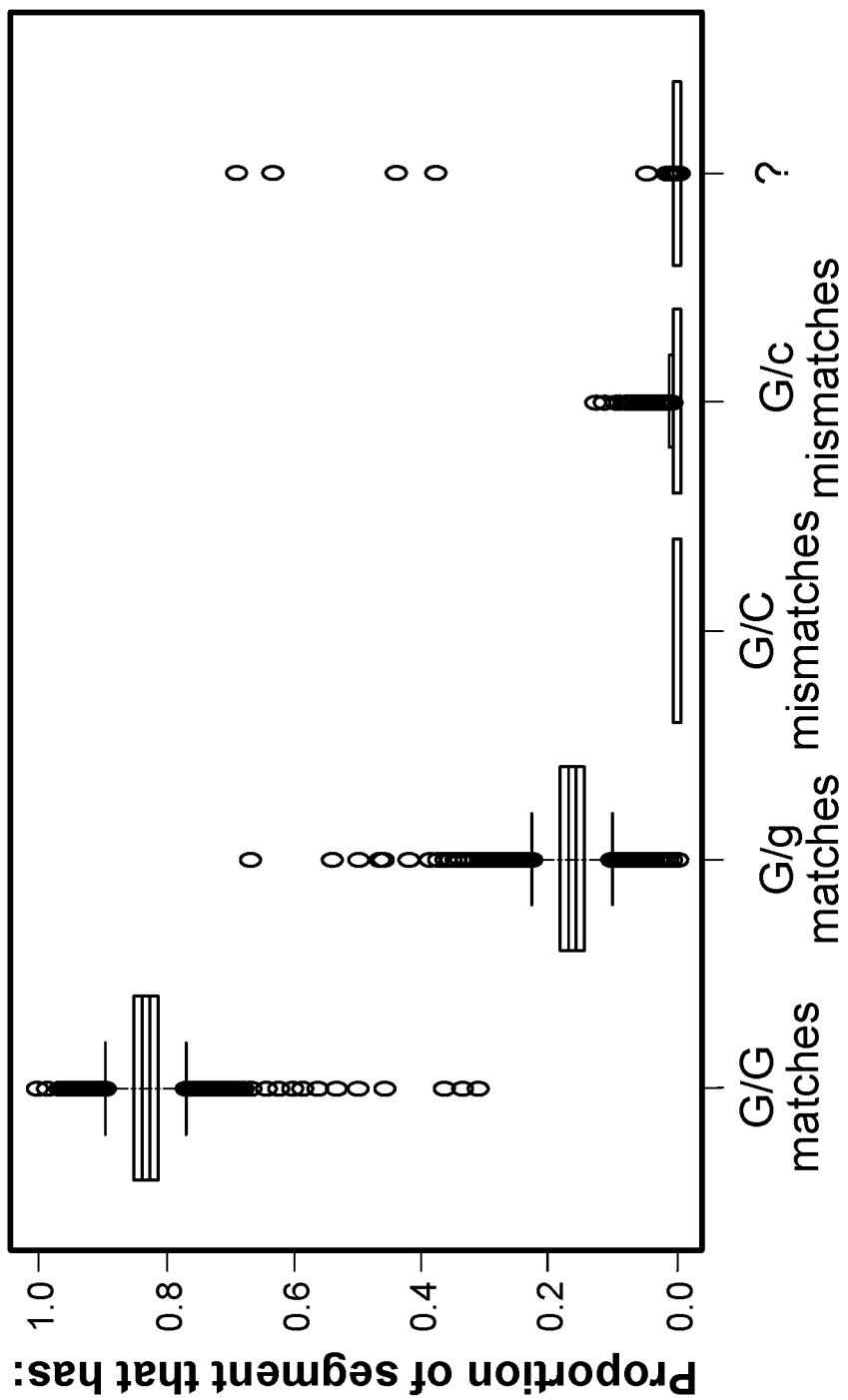
FIG. 7 shows the results of haplotype inference given inferred phase and true IBD endpoints.

Inferred phase, true IBD endpoints: When phase is inferred, lower-case mismatches are found in the haplotype inference. This is due to minor inaccuracies in phase estimation. FIG. 7 shows the results of haplotype inference given inferred phase and true IBD endpoints. G/G matches and G/g matches denote upper- and lower-case matches, respectively; G/C mismatches and G/c mismatches denote upper- and lower-case mismatches, respectively.

This has implications for the stitching algorithm: some amount of lower-case mismatches should be allowed when assessing identity (as described herein).

Figure 8:
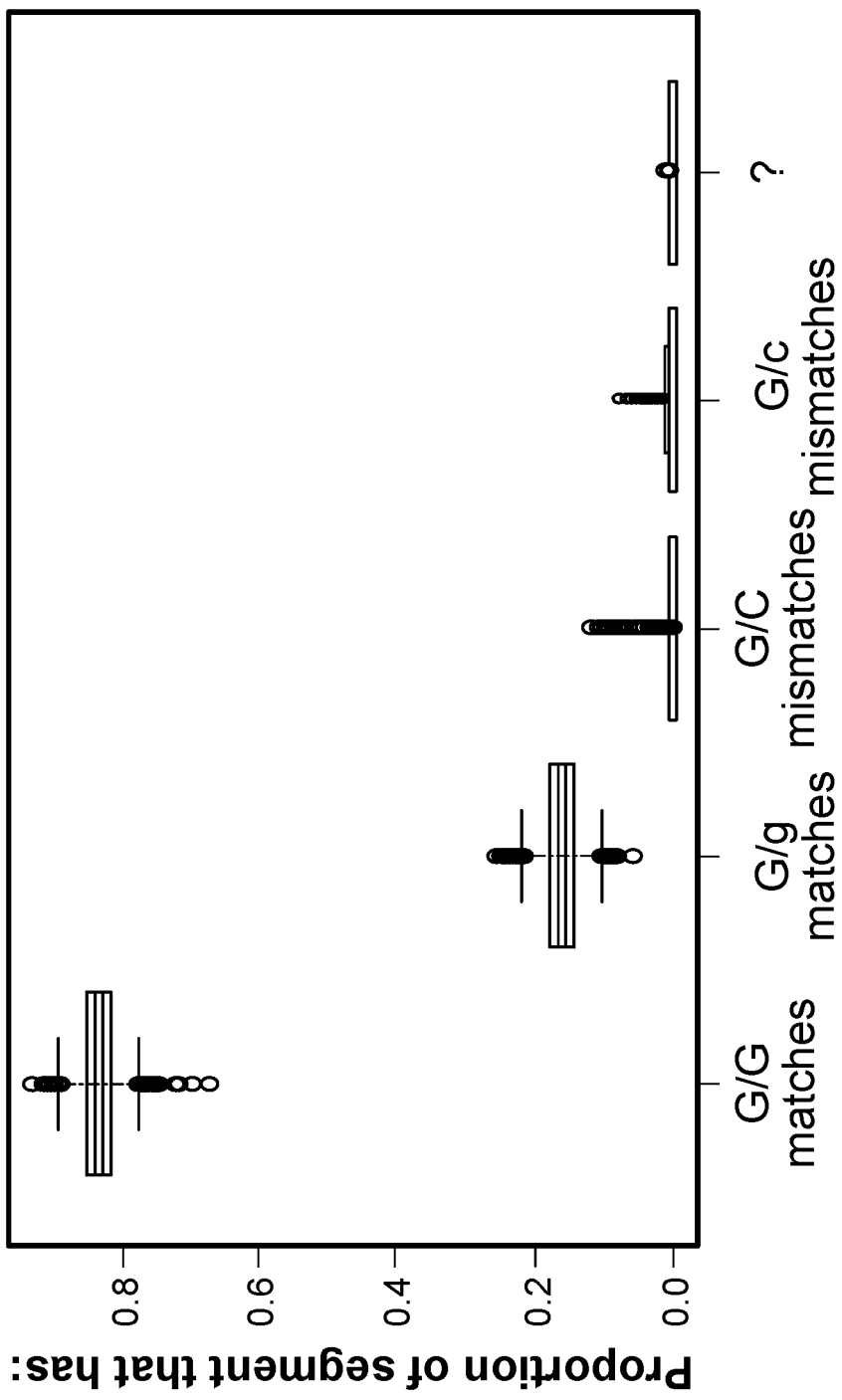
FIG. 8 show the results of haplotype inference given inferred phase and inferred IBD endpoints.

Inferred phase, inferred IBD endpoints: when IBD is inferred, more upper-case mismatches are identified due to errors in IBD estimation. FIG. 8 show the results of haplotype inference given inferred phase and inferred IBD endpoints. G/G matches and G/g matches denote upper- and lower- case matches, respectively; G/C mismatches and G/c mismatches denote upper- and lower- case mismatches, respectively. Note that when IBD is inferred using JERM-LINE or GERMLINE, a 5 cM cutoff is imposed.

Figure 9:
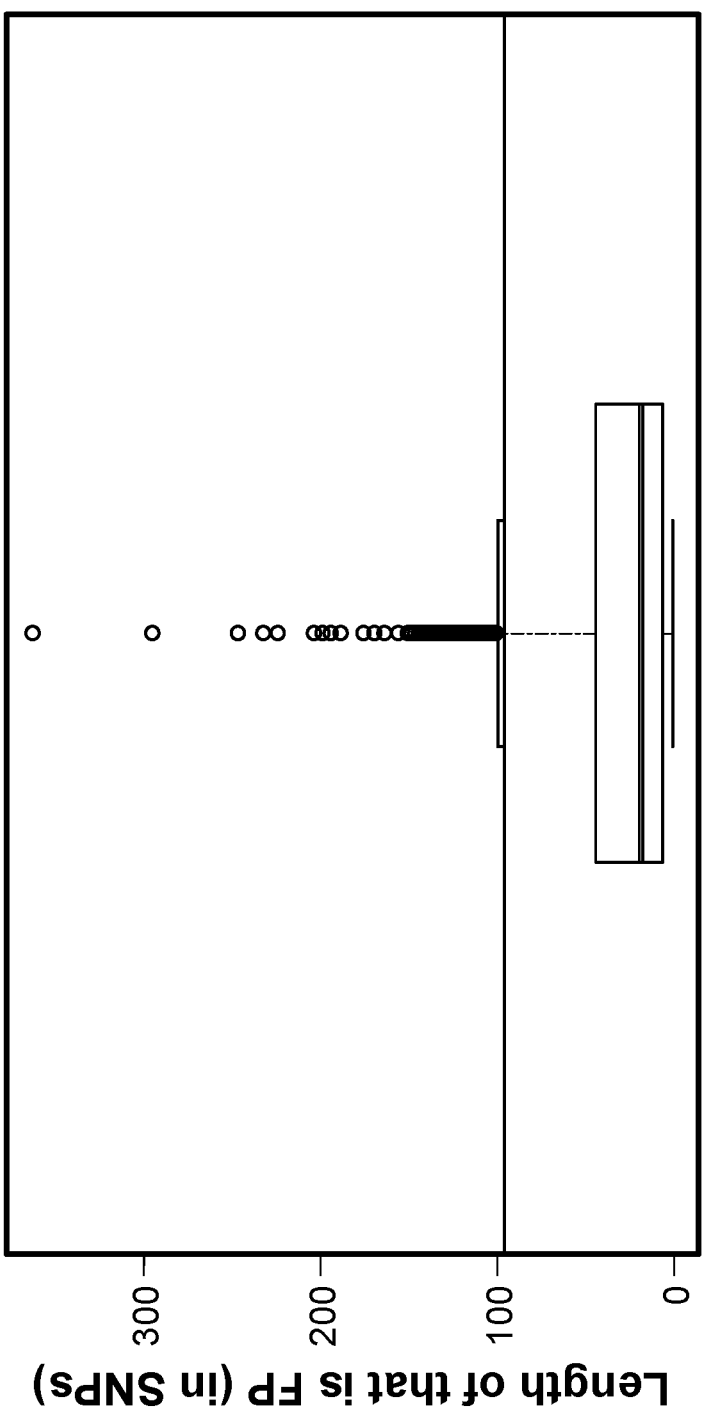
FIG. 9 illustrates lengths of inferred IBD segments (in SNPs) that are false positive.

FIG. 9 illustrates lengths of inferred IBD segments (in SNPs) that are false positive. FIG. 9 demonstrates that in this case, most errors in inferred IBD segments occur at the endpoints of the segments themselves. The false positive segments also generally span less than one 96 SNP window (the window size used for GERMLINE).

Figure 10:
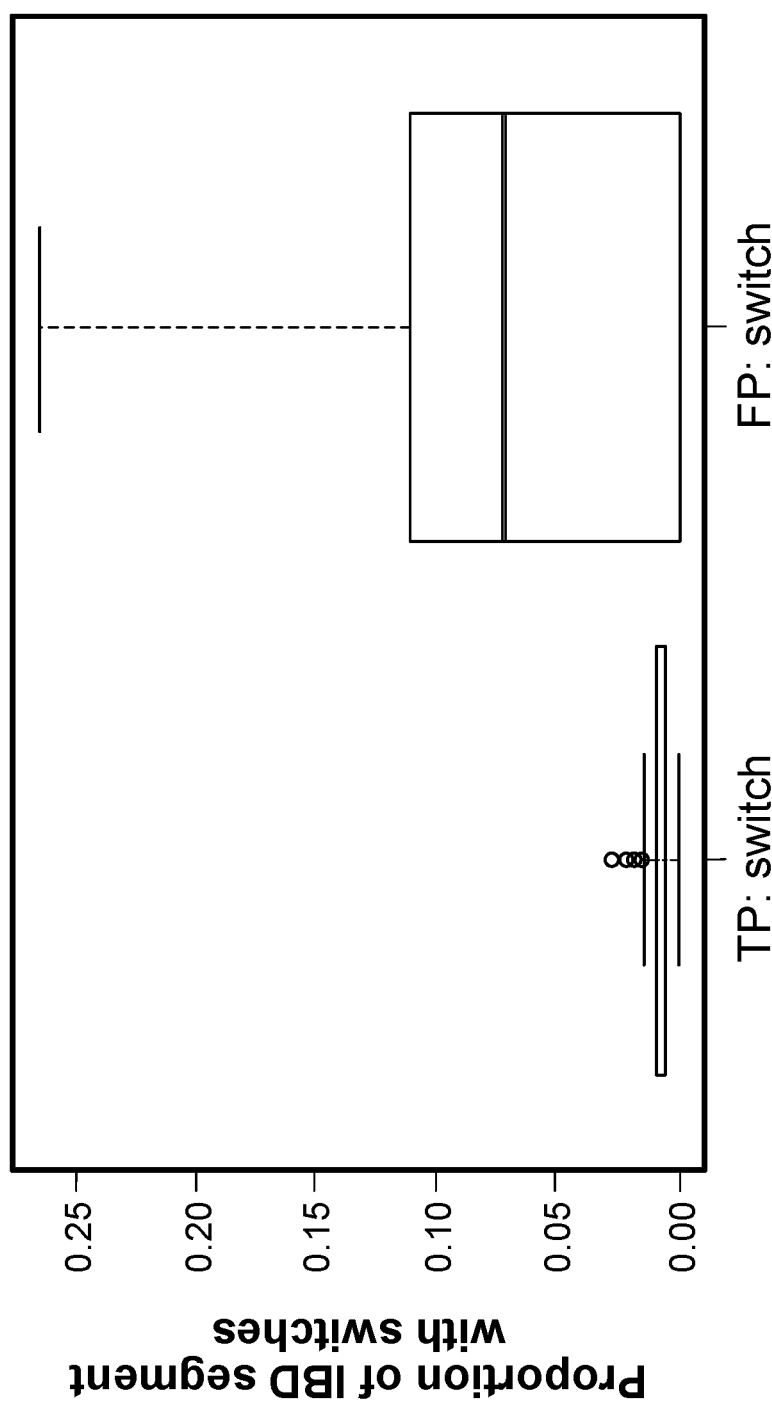
FIG. 10 illustrates a rate of switching among phased haplotypes.

In addition, the number of phase flips necessary to make the inferred haplotypes consistent with the phase of each individual (as described above) was assessed. As shown in FIG. 10, the number of switches required to make the haplotype of a match consistent with the phased haplotypes is an order of magnitude larger in false positive regions of IBD segments than true positive IBD regions. FIG. 10 illustrates a rate of switching among phased haplotypes is an order of magnitude larger in false positive than in true positive regions of an IBD segment.

B. Stitching

Below is described the details of the stitching algorithm that was used in this particular application 1. Pre-filtering segments added to model: All IBD segments between individuals whose MRCA is the couple of interest are included. For inferred IBD segments, a length threshold of 5 cM is imposed (see above).
2. Ordering: Segments are ordered from left to right along each chromosome, and further ordered by length.
3. Scores of stitched paths: The score of each path is the summed cM length of segments involved in the path.
4. Criteria for segment overlap: Any amount of segment overlap is allowed.
5. Criteria for "identity": An unknown allele ("?") is defined as identical to all other letters (both upper and lower case). Any number of mismatches at lower case letters are allowed (i.e. "G" defined as identical to lower-case "c"; and lower-case "g" defined as identical to lower-case "c"). No upper-case mismatches allowed in this step. [0001] When applying the method to simulated data (see Results), allowing a small number of lower-case mismatches generally provides good performance (i.e a combination of i), ii) and iii) above; see Results).
6. Updating/modifying existing paths: The IBD segments that comprise the paths are not persisted; as described above.
7. Account for multiple matching paths: When an IBD segment matches multiple existing paths, select the path with the highest score, as described above.
8. Post-merging of paths: After all IBD segments are added to the model, post-processing is performed to allow any number of upper-case mismatches among paths, and merge them (when IBD is inferred).
9. Select high-quality paths: In this application, all paths are selected.

After applying the stitching algorithm, two statistics are calculated based on the true known data from the simulations: precision and recall. Precision is the proportion of stitched paths that represent one of the true ancestral haplotypes in their entirety. Recall is the proportion of the true ancestral genomes (that are covered by IBD segments among their descendants; see Section C below and FIG. 13) that are represented by the stitched paths.

Figure 11:
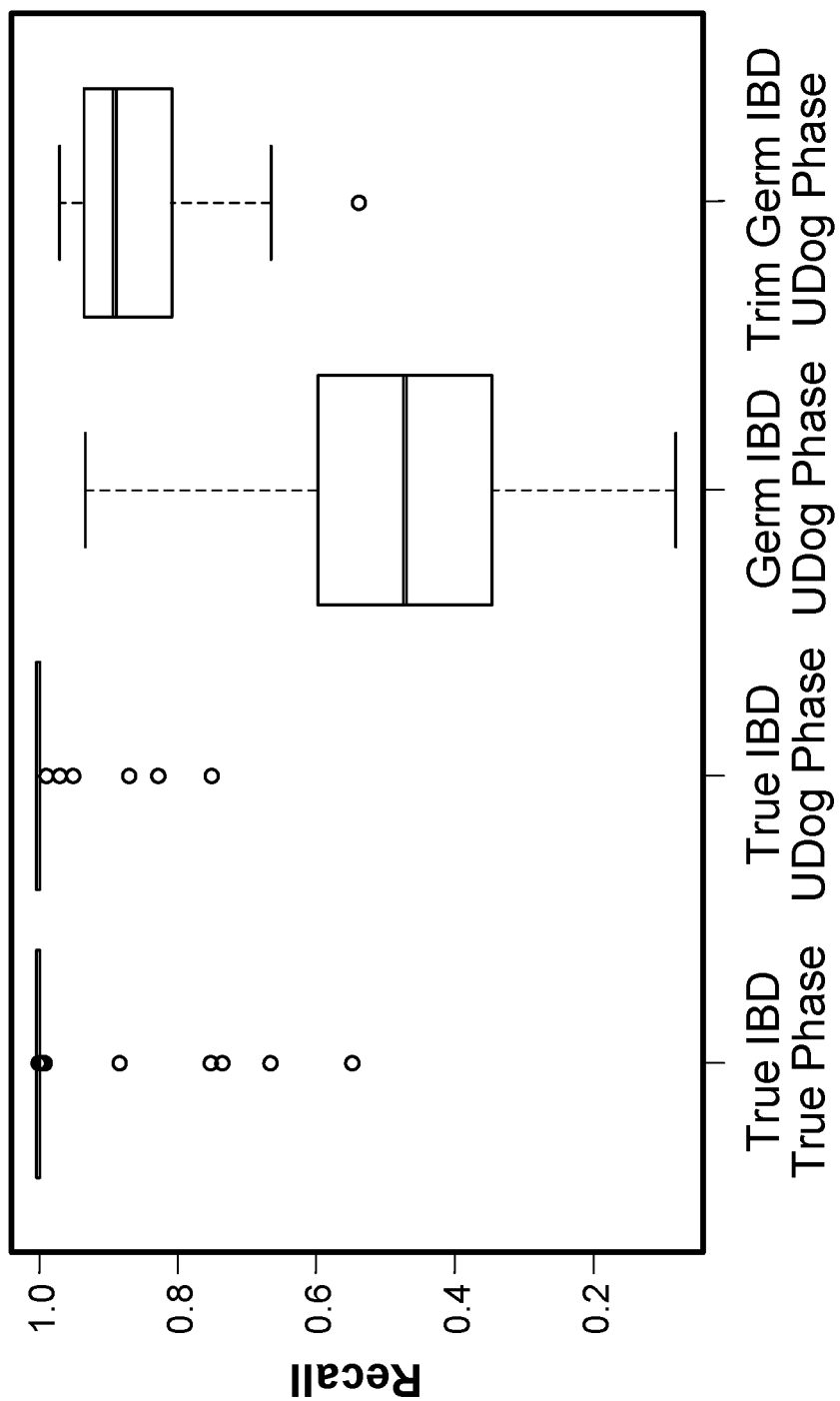
FIG. 11 illustrates recall using various versions of simulated data as described in the Example.
Figure 12:
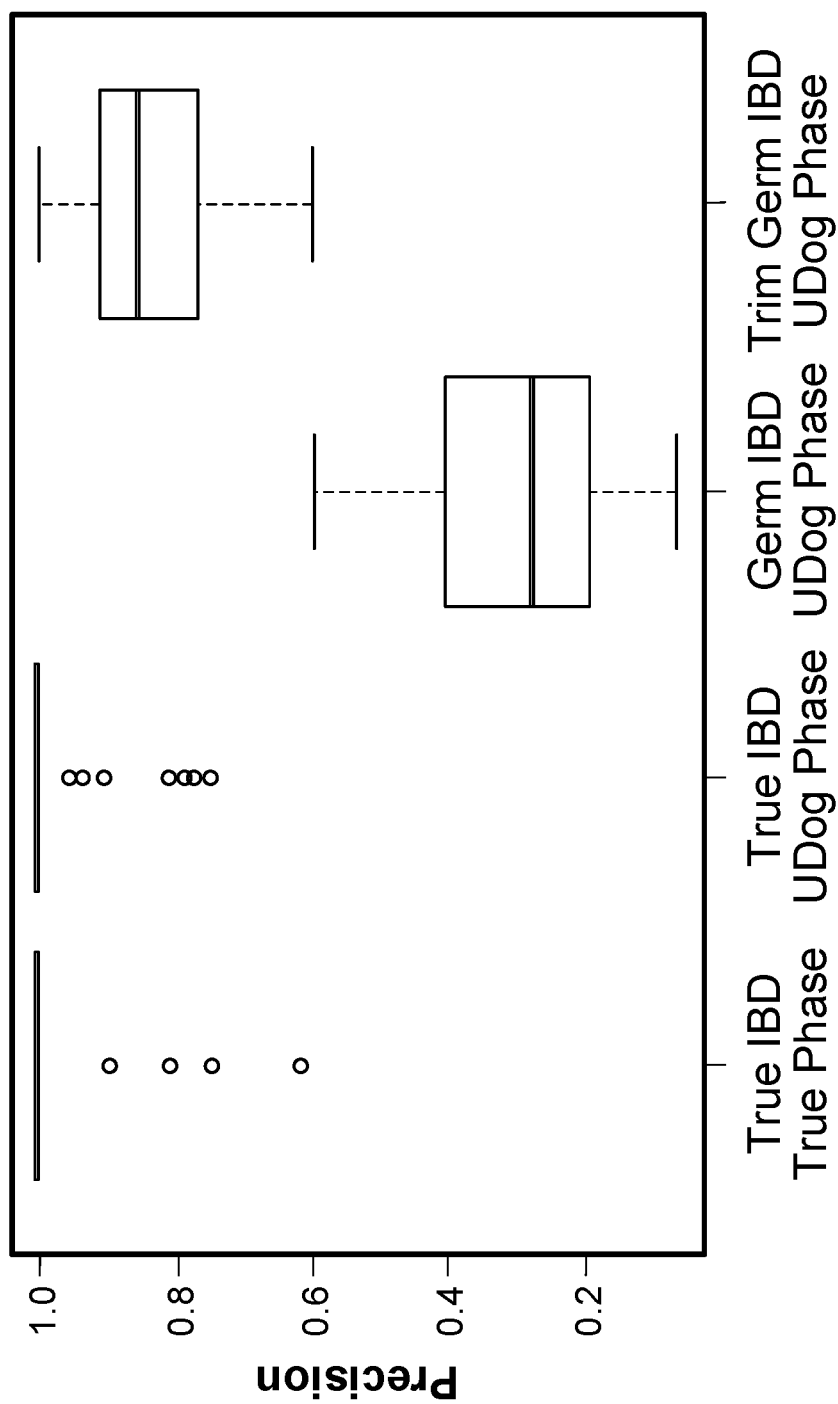
FIG. 12 illustrates precision using various versions of simulated data as described in the Example.

FIGS. 11 and 12 below show boxplots of the precision and recall (as defined above) for the stitching algorithm across 22 chromosomes, each with 10 random independent simulations each. Different columns of the plots show the metrics using the 4 sets of data described above (true phase, true IBD; Inferred phase, true IBD; inferred phase, inferred IBD; inferred phase, inferred IBD with trimmed endpoints).

Precision and recall for the stitching algorithm are close to 100% for true IBD when phase is both true and inferred with UnderDog (see FIG. 11 and FIG. 12). When there are inaccuracies in IBD estimation, precision and recall decrease dramatically (see FIGS. 11 and 12). However, when inaccuracies in IBD estimation are minimized by trimming the endpoints of IBD segments (based on the observation in FIG. 9), precision and recall again increase to above 80% on average.

The results on this particular test dataset demonstrate the utility of the haplotype inference and stitching algorithms. While these particular examples only are based on one parameter combination of the stitching algorithm, it demonstrates that various other parameter combinations can be effective. It should also be noticed that just as accuracy in these approaches decreases when IBD accuracy decreases, accuracy thus would also naturally decrease with inaccuracies in pedigree information (not simulated). Thus, scores described above can be used to further filter IBD segments or stitched ancestral haplotypes.

C. Theoretical Reconstruction Maxima

Finally, the applicability of this IBD-based stitching method is dependent upon the structure of the true pedigree of the ancestor and his or her descendants. To address this point, simulations were performed of various pedigree shapes (an example shown in FIG. 6C) to assess the theoretical maximum recall for reconstruction of an ancestral genome (see FIG. 11 for recall on real data).

Figure 13:
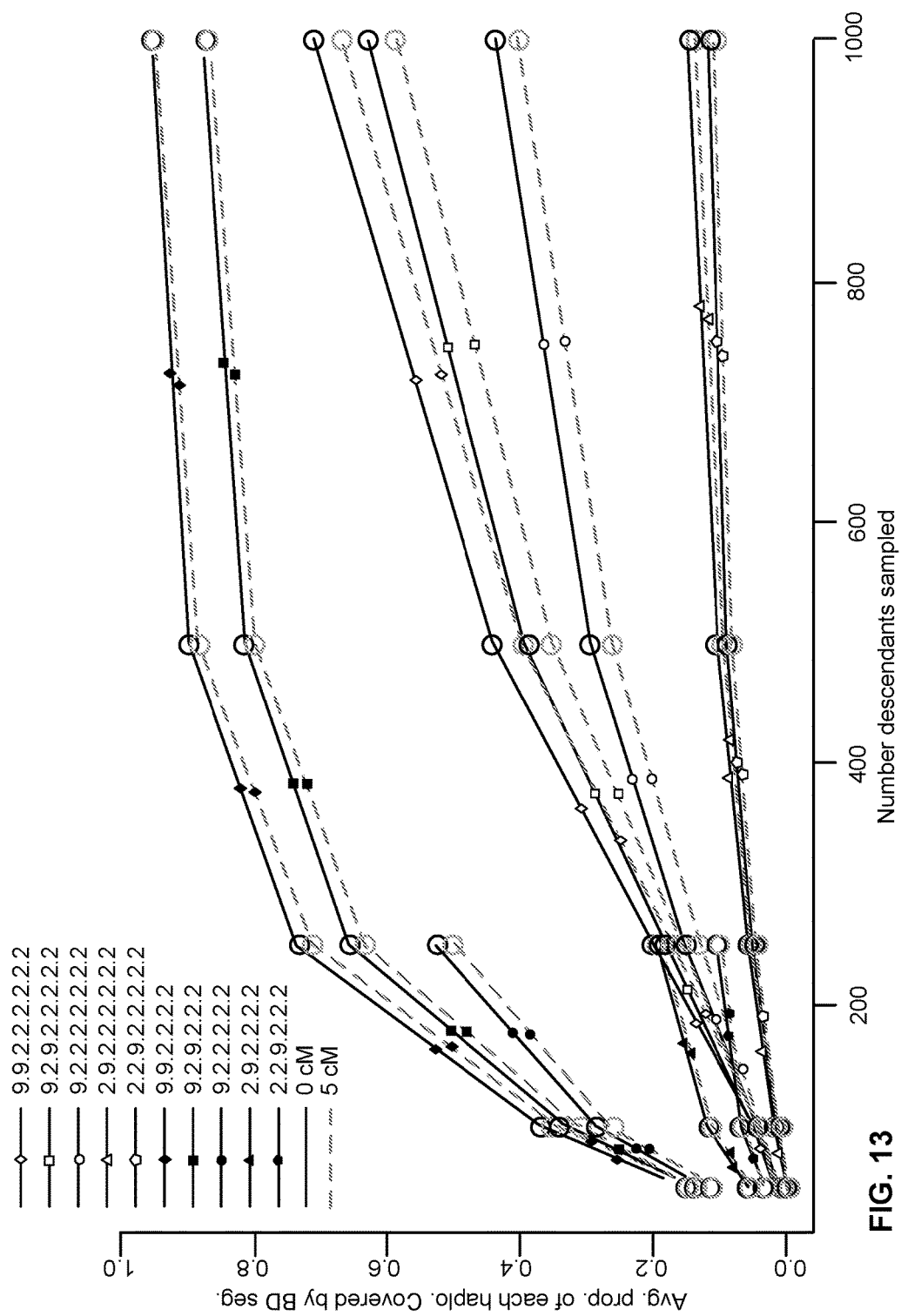
FIG. 13 illustrates a proportion of ancestral chromosomes that are covered by true IBD segments among a set of descendants for various numbers of sampled descendants and various pedigree shapes as described in the Example.

FIG. 13 illustrates a proportion of ancestral chromosomes that are covered by true IBD segments among a set of descendants for various numbers of sampled descendants and various pedigree shapes. Pedigrees of various shapes are shown—for example, 9.9.2.2.2.2.2.2 indicates an 8 generation pedigree, starting with a couple who has 9 children, who each have 9 children, who each have 2 children for the remaining 6 generations. Dashed lines indicate an IBD segment length threshold of 5 cM. The simulations reveal that the theoretical maximum for the amount of genome that can be reconstructed greatly depends on the shape of the pedigree. For example, more of the genome can theoretically be reconstructed for ancestors who have a large number of children in the preliminary generations of their pedigree. For an ancestor of interest who has a known general pedigree structure, simulations such as those described can be used to determine the amount of the genome that could theoretically be reconstructed in the proposed manner given some number of sampled descendants (as an upper bound on recall).

This example demonstrates successful reconstruction of the genomes of a set of ancestors from IBD segments inferred among their descendants, given pedigree and genetic information.

REFERENCES

B L Browning and S R Browning (2009) A unified approach to genotype imputation and haplotype phase inference for large data sets of trios and unrelated individuals. Am J Hum Genet 84:210-223.

Elston and Stewart (1971). A general model for the genetic analysis of pedigree data. Human Heredity 21(6).

Gusev A, Lowe J K, Stoffel M, Daly M J, Altshuler D, Breslow J L, Friedman J M, Pe'er I (2008) Whole population, genomewide mapping of hidden relatedness. Genome Research.

Kong et al. (2008) Detection of sharing by descent, long-range phasing and haplotype imputation. Nature Genetics 40 (9) 1068-1075.

Lander and Green (1987). Construction of multilocus genetic linkage maps in humans. PNAS 84, 2363-2367.

Meuwissen and Goddard (2010). The use of family relationships an linkage disequilibrium to impute phase and missing genotypes in upt o whole-genome sequence density genotypic data. Genetics 185: 1441-9.

Ott (1974). Estimation of the recombination fraction in human pedigrees: efficient computation of the likelihood for human linkage studies. American Journal of Human Genetics, 26(5), 588-97.

Thompson, E. A. (2000). Statistical inference from genetic data on pedigrees.

The invention claimed is:

1. A method for reconstructing at least one phased chromosomal haplotype of at least one genomic segment of an ancestral couple of interest, the method comprising
receiving, by a computer, genetic data for a plurality of individuals;
analyzing, by the computer, the genetic data to identify a genomic DNA segment that is identical by descent (IBD) among pairs of the individuals, the IBD genomic DNA segment identified by chromosome number and start and end coordinates, thereby identifying a set of pairs of individuals each pair sharing at least one IBD genomic DNA segment;
receiving, by the computer, pedigree data for the set;
analyzing, by the computer, the pedigree data to identify a most recent common ancestor (MRCA) of at least one of the pairs of individuals in the set, the MRCA belonging to the ancestral couple;
for one of the IBD genomic DNA segments shared by one of the pairs of individuals, comparing, by the computer, phased haplotypes of the pair of individuals to determine an inferred IBD haplotype;
generating a plurality of inferred IBD haplotypes based on other phased haplotypes of other pairs of individuals in the set; and
stitching together the inferred IBD haplotypes, by the computer, to generate stitched ancestral haplotypes reconstructing the at least one phased chromosomal haplotype of at least one genomic segment of the ancestral couple of interest.

2. The method of claim 1, the stitching comprising:
ordering, by the computer, the inferred IBD haplotypes;
comparing, by the computer, each inferred IBD haplotype to a next inferred IBD haplotype to generate an identity score; and
creating, by the computer, a stitched ancestral haplotype by updating and extending if the identity score meets a threshold to generate a set of stitched ancestral haplotypes.

3. The method of claim 2, the inferred IBD haplotypes prefiltered by IBD genomic DNA segment length, Family Network algorithm score, and/or number of common ancestors.

4. The method of claim 2, the inferred IBD haplotypes ordered by chromosomal location, segment length, amount of overlap, and/or Family Network algorithm score.

5. The method of claim 2, the identity score including amount of overlap and/or amount of identical sequences.

6. The method of claim 2, further comprising ranking the stitched ancestral haplotype based on quantity of IBD genomic DNA segments involved in the stitched ancestral haplotype, total length of IBD genomic DNA segments involved in the stitched ancestral haplotypes, total Family Network algorithm score of IBD genomic DNA segments, total score based on recent common ancestor, total amount of overlap of stitched ancestral haplotypes and/or total amount of identity of stitched ancestral haplotypes.

7. The method of claim 1, wherein the genetic data comprises genotyping of at least 700,000 single nucleotide polymorphisms (SNPs).

8. The method of claim 1, wherein the genetic data comprises single nucleotide polymorphisms (SNPs) data, partial sequence data, complete sequence data, exome data, restriction fragment length polymorphism (RFLP) data, copy number variant data, or indel data.

9. The method of claim 1, wherein the plurality of individuals belongs to a Family Network.

10. The method of claim 1, wherein the pedigree data does not include data for all individuals in the set.

11. The method of claim 1, wherein analyzing the genetic data comprises a) phasing each individual's genotype; and b) inferring at least one genomic DNA segment that is identical by descent (IBD) among at least two individuals.

12. The method of claim 1, wherein identifying the MRCA comprises using the pedigree data and Family Networks methods.

13. A non-transitory computer-readable medium comprising computer-executable instructions for reconstructing at least one phase chromosomal haplotype of at least one genomic segment of an ancestral couple of interest, the instructions, when executed by one or more processors, cause the one or more processors to:
receive, by a computer, genetic data for a plurality of individuals;
analyzing, by the computer, the genetic data to identify a genomic DNA segment that is identical by descent (IBD) among pairs of the individuals, the IBD genomic DNA segment identified by chromosome number and start and end coordinates, thereby identifying a set of pairs of individuals each pair sharing at least one IBD genomic DNA segment;
receive, by the computer, pedigree data for the set;
analyze, by the computer, the pedigree data to identify a most recent common ancestor (MRCA) of at least one of the pairs of individuals in the set, the MRCA belonging to the ancestral couple;
for one of the IBD genomic DNA segments shared by one of the pairs of individuals, comparing, by the computer, phased haplotypes of the pair of individuals to determine an inferred IBD haplotype;
generate a plurality of inferred IBD haplotypes based on other phased haplotypes of other pairs of individuals in the set; and
stitch together the inferred IBD haplotypes, by the computer, to generate stitched ancestral haplotypes reconstructing the at least one phased chromosomal haplotype of at least one genomic segment of the ancestral couple of interest.

14. The non-transitory, computer readable medium of claim 13, further comprising instructions to:
   order, by the computer, the inferred IBD haplotypes;
   compare, by the computer, each inferred IBD haplotype to a next inferred IBD haplotype to generate an identity score; and
   create, by the computer, a stitched ancestral haplotype by updating and extending if the identity score meets a threshold to generate a set of stitched ancestral haplotypes.

15. The non-transitory, computer readable medium of claim 14, wherein the identity score including amount of overlap and/or amount of identical sequences.

16. The non-transitory, computer readable medium of claim 14, further comprising instructions to rank the stitched ancestral haplotype based on quantity of IBD genomic DNA segments involved in the stitched ancestral haplotype, total length of IBD genomic DNA segments involved in the stitched ancestral haplotypes, total Family Network algorithm score of IBD genomic DNA segments, total score based on recent common ancestor, total amount of overlap of stitched ancestral haplotypes and/or total amount of identity of stitched ancestral haplotypes.

17. The non-transitory, computer readable medium of claim 13, wherein the genetic data comprises genotyping of at least 700,000 single nucleotide polymorphisms (SNPs).

18. The non-transitory, computer readable medium of claim 13, wherein the genetic data comprises single nucleotide polymorphisms (SNPs) data, partial sequence data, complete sequence data, exome data, restriction fragment length polymorphism (RFLP) data, copy number variant data, or indel data.

19. The non-transitory, computer readable medium of claim 13, further comprising instructions to analyze the genetic data using: a) phasing each individual's genotype; and b) inferring at least one genomic DNA segment that is identical by descent (IBD) among at least two individuals.

20. The non-transitory, computer readable medium of claim 13, wherein identifying the MRCA comprises using the pedigree data and Family Networks methods.

* * * * *